US012635864B2

(12) United States Patent
Horie et al.

(10) Patent No.: US 12,635,864 B2
(45) Date of Patent: May 26, 2026

(54) BENDING TUBE, INSERTION APPLIANCE, AND MANUFACTURING METHOD OF BENDING TUBE

(71) Applicant: OLYMPUS MEDICAL SYSTEMS CORP., Tokyo (JP)

(72) Inventors: Satoshi Horie, Kokubunji (JP); Eijiro Sato, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 308 days.

(21) Appl. No.: 18/232,499

(22) Filed: Aug. 10, 2023

(65) Prior Publication Data

US 2024/0138660 A1 May 2, 2024

Related U.S. Application Data

(60) Provisional application No. 63/399,560, filed on Aug. 19, 2022.

(51) Int. Cl.
*A61B 1/005* (2006.01)
*A61B 1/00* (2006.01)
(Continued)

(52) U.S. Cl.
CPC .......... *A61B 1/0056* (2013.01); *A61B 1/0011* (2013.01); *A61B 1/0057* (2013.01);
(Continued)

(58) Field of Classification Search
CPC . A61B 1/0056; A61B 1/00103; A61B 1/0011; A61B 1/0057; A61B 1/008; A61B 1/0055; A61M 25/0013; A61M 25/0138
See application file for complete search history.

(56) References Cited

U.S. PATENT DOCUMENTS

| 8,967,204 B2 | 3/2015 | Konstorum et al. |
| 9,820,635 B2 | 11/2017 | Seto et al. |

(Continued)

FOREIGN PATENT DOCUMENTS

| JP | 2005-007068 A | 1/2005 |
| JP | 2016-190043 A | 11/2016 |

(Continued)

*Primary Examiner* — Michael J Carey
*Assistant Examiner* — Olivia Grace Starkey
(74) *Attorney, Agent, or Firm* — Morgan, Lewis & Bockius LLP

(57) ABSTRACT

A bending tube of an insertion appliance includes a first region including a first plurality of slits, a second region provided proximally relative to the first region and including a second plurality of slits, and a guiding surface on an inner circumferential surface of the bending tube, the guiding surface extending in a circumferential direction, and including a channel configured to slidably house a wire. Each slit of the first plurality of slits is at different position in the circumferential direction, and at different positions in a longitudinal direction. Each slit of the second plurality of slits is provided at different position in the circumferential direction, and at different position in the longitudinal direction. The first plurality of slits is distributed over a first angle in the circumferential direction, and the second plurality of slits is distributed over a second angle smaller than the first angle in the circumferential direction.

19 Claims, 12 Drawing Sheets

(51) Int. Cl.
    *A61M 25/00*         (2006.01)
    *A61M 25/01*         (2006.01)

(52) U.S. Cl.
    CPC ...... *A61B 1/00103* (2013.01); *A61M 25/0013*
              (2013.01); *A61M 25/0138* (2013.01)

(56) References Cited

U.S. PATENT DOCUMENTS

| | | | | |
|---|---|---|---|---|
| 2007/0135803 | A1* | 6/2007 | Belson ............... | A61B 1/00154 |
| | | | | 606/1 |
| 2007/0282358 | A1* | 12/2007 | Remiszewski ....... | A61B 1/0057 |
| | | | | 606/159 |
| 2013/0085442 | A1 | 4/2013 | Shtul et al. | |
| 2016/0302762 | A1 | 10/2016 | Stigall et al. | |
| 2017/0095138 | A1 | 4/2017 | Nakade et al. | |
| 2017/0150879 | A1* | 6/2017 | Matsuura .......... | A61M 25/0147 |
| 2021/0386443 | A1* | 12/2021 | Heimberger ......... | A61B 1/0057 |
| 2022/0338718 | A1* | 10/2022 | Van Ness ............. | A61B 1/0055 |
| 2023/0172440 | A1* | 6/2023 | Schütz ............... | A61B 1/00045 |
| | | | | 600/109 |

FOREIGN PATENT DOCUMENTS

| | | | |
|---|---|---|---|
| JP | 2018-512961 | A | 5/2018 |
| JP | 2022-020248 | A | 2/2022 |
| JP | 2023-002946 | A | 1/2023 |
| WO | 2014/030437 | A1 | 2/2014 |
| WO | 2015/125334 | A1 | 8/2015 |
| WO | 2016/052145 | A1 | 4/2016 |
| WO | 2016/167099 | A1 | 10/2016 |
| WO | 2018/236513 | A1 | 12/2018 |

* cited by examiner

| BENDING DIRECTION | WIRES TO BE PULLED |
|---|---|
| U | W1+W3 |
| R | W1+W2 |
| D | W2+W3 |
| L | W1+W3 |

| | EXAMPLE OF BENDING IN L DIRECTION |
|---|---|
| 1 (SEEN FROM L DIRECTION) | |
| 2 (SEEN FROM D DIRECTION) | |

MANUFACTURING OF BENDING TUBE

DISPOSE GUIDING SHAPE PORTION — S1

FORM FIRST SLOT
BY LASER PROCESSING — S2

FORM SECOND SLOT
BY LASER PROCESSING — S3

END

BENDING TUBE, INSERTION APPLIANCE, AND MANUFACTURING METHOD OF BENDING TUBE

RELATED APPLICATION DATA

This application is based on and claims priority under 35 U.S.C. § 119 to U.S. Provisional Application No. 63/399,560 filed on Aug. 19, 2022, the entire contents of which are incorporated herein by reference.

FIELD OF DISCLOSURE

The present disclosure relates to a bending tube, an insertion appliance including the bending tube, and a manufacturing method of the bending tube.

BACKGROUND

There already exists an insertion appliance, such as an endoscope, that includes a bendable bending portion on a distal end side of an insertion section.

For example, International Publication No. WO2015/125334 describes a bending tube that is disposed in a bending portion of an endoscope. The bending tube is formed by providing a plurality of slots (slits) in a metal bending tube main body, in a longitudinal axis direction.

The publication describes that a pitch between slots is made different between a distal end side and a proximal end side of the bending tube.

The bending portion is bent in four directions of up, down, left, and right, for example, by pulling bending operation wires as long members. A typical bending portion includes four bending operation wires corresponding to bending in four directions of up (U), down (D), left (L), and right (R).

Meanwhile, a diameter of an endoscope is desired to be reduced. Wires and guiding shape portions through which the wires are inserted, provided in an insertion section, occupy a relatively large area when seen along a cross-section that is perpendicular to a longitudinal axis of the insertion section.

Accordingly, in relation to an endoscope such as a pyelou-reteroscope where reduction in the diameter is particularly desired, it is proposed to reduce the number of bending operation wires from four to three to reduce the diameter of the bending tube. In this case, to bend the bending portion in one of four directions, two bending operation wires, among the three bending operation wires, are selectively pulled.

With the pyeloureteroscope, a maximum bending angle exceeding 180 degrees is sometimes secured for the bending portion such that observation of inside of a subject is performed without missing stones and the like, for example.

Accordingly, for example, there is a case where slots that allow bending in four directions of up, down, left, and right are provided on a distal end side of a bending tube, and slots that allow bending in two directions of up and down are provided on a proximal end side of the bending tube, where a maximum bending angle in an up-down direction that is a main bending direction exceeds 180 degrees (a maximum bending angle in a left-right direction that is a sub-bending direction may be less than 180 degrees).

SUMMARY

A bending tube of an insertion appliance according to an aspect of the present disclosure includes a first region including a first plurality of slits, a second region provided proximally relative to the first region, the second region including a second plurality of slits, and a guiding surface on an inner circumferential surface of the bending tube, the guiding surface extending in a circumferential direction of the bending tube, and including a channel configured to slidably house a wire for bending the bending tube. Each slit of the first plurality of slits is provided at different position in the circumferential direction, and at different position in a longitudinal direction of the bending tube. Each slit of the second plurality of slits is provided at different position in the circumferential direction, and at different position in the longitudinal direction. The first plurality of slits is distributed over a first angle in the circumferential direction, and the second plurality of slits is distributed over a second angle in the circumferential direction. The second angle is smaller than the first angle.

A manufacturing method of a bending tube of an insertion appliance according to an aspect of the present disclosure includes providing a first guiding surface, a second guiding surface, and a third guiding surface on an inner circumferential surface of the bending tube. The first guiding surfaces, the second guiding surface, and the third guiding surface, are distributed in a circumferential direction of the bending tube. The first guiding surface includes a first channel configured to slidably house a first wire for bending the bending tube, the second guiding surface includes a second channel configured to slidably house a second wire for bending the bending tube, and the third guiding surface includes a third channel configured to slidably house a third wire for bending the bending tube. The method further includes providing, in a first region of the bending tube, a first plurality of slits, each slit of the first plurality of slits at different positions in the circumferential direction, and at different positions in a longitudinal direction of the bending tube, and providing, in a second region of the bending tube, a second plurality of slits, each slit of the second plurality of slits is at different positions in the circumferential direction, and at different positions in the longitudinal direction The second region is provided proximally relative to the first region. The first plurality of slits is distributed over a first angle in the circumferential direction, and the second plurality of slits is distributed over a second angle. The second angle is smaller than the first angle in the circumferential direction.

DETAILED DESCRIPTION

Hereinafter, an embodiment of the present disclosure will be described with reference to the drawings. However, the present disclosure is not limited by the embodiment described below.

Note that in the description of the drawings, the same or corresponding elements are denoted by the same reference sign as appropriate. Furthermore, the drawings are schematic, and a relationship between lengths of elements, a ratio of lengths of elements, the number of each element, and the like in one drawing may be different from actual relationship, ratio, number, and the like for the sake of simplicity of the description. Moreover, a plurality of drawings may include portions having different relationships or ratios in relation to lengths.

First Embodiment

Figure 1A:
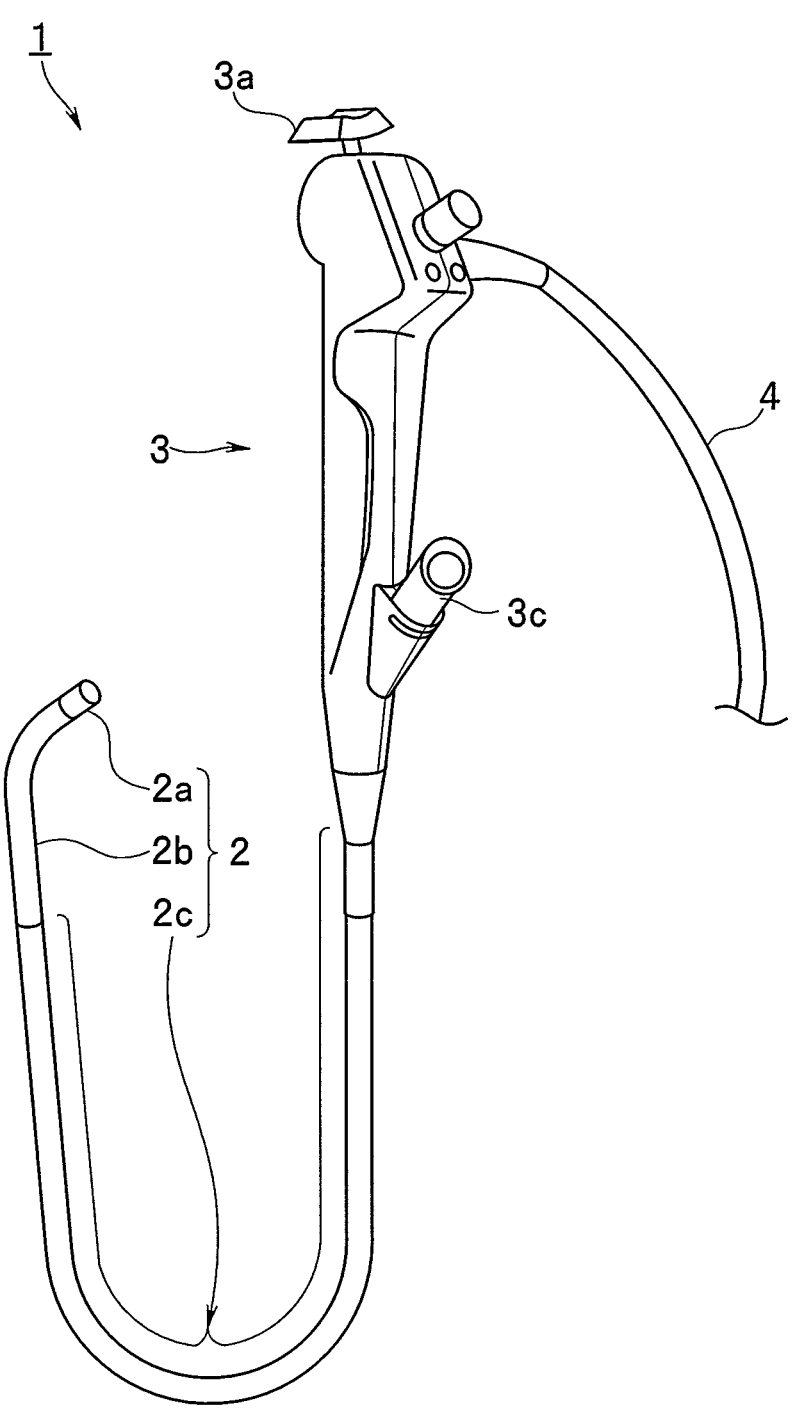
FIG. 1A is a perspective view showing an example configuration of an endoscope to which a bending tube of a first embodiment is applied.

FIGS. 1A to 10 show a first embodiment. FIG. 1A is a perspective view showing an example configuration of an endoscope 1 to which a bending tube 11 of the first embodiment is applied. FIG. 1B is a perspective view showing, in an exploded manner, an internal structure of an operation section of the endoscope to which the bending tube of the first embodiment is applied.

The present embodiment describes the endoscope 1 as an insertion appliance that includes a bending portion 2b that is formed by the bending tube 11 of the first embodiment. A more specific example of the endoscope 1 is a pyelouret-eroscope that is an electronic endoscope including an image pickup unit including an image pickup device. Note that the pyeloureteroscope may be a fiberscope including a fiber. Moreover, the endoscope 1 is not limited to the pyelouret-eroscope, and may instead be a more general endoscope. Furthermore, the insertion appliance is not limited to the endoscope 1, and may instead be a treatment instrument that is bendable, for example.

As shown in FIG. 1A, the endoscope 1 includes an insertion section 2, an operation section 3, and a universal cord 4. The endoscope 1 may be a single-use endoscope that is disposed of after being used once. A single-use endoscope may also be collected after use and be reused after being cleaned/inspected/repaired by a manufacturer from the standpoint of economical use of resources.

An image guide, a bending operation wire 19 (see FIGS. 2, 4, and the like), a treatment instrument channel, and the like are inserted in the insertion section 2 and the operation section 3 of the endoscope 1. Furthermore, a light guide, a power cable, a signal cable, and the like are inserted in the insertion section 2, the operation section 3, and the universal cord 4 of the endoscope 1.

The insertion section 2 is a tubular portion that is inserted inside a subject. The insertion section 2 includes a distal end portion 2a, a bending portion 2b, and a flexible tube portion 2c in the stated order from a distal end side toward a proximal end side.

The distal end portion 2a includes an illumination optical system, an observation optical system, a distal end-side opening of the treatment instrument channel, and the like. The illumination optical system radiates illumination light transmitted by the light guide, on a subject. The observation optical system receives return light from the subject irradiated by the illumination light, and forms an optical image of the subject on an image pickup device of an image pickup unit 26 (see FIG. 12 and the like). When a treatment instrument is inserted in the treatment instrument channel, a distal end side of the treatment instrument protrudes from the distal end-side opening of the treatment instrument channel.

The bending portion 2b is a bendable portion that is provided on a proximal end side of the distal end portion 2a. The flexible tube portion 2c is longer than the distal end portion 2a and the bending portion 2b. Accordingly, the bending portion 2b is provided on a distal end side of the insertion section. The bending portion 2b is bent by pulling the bending operation wire 19.

The bending portion 2b is bendable in four directions. The four directions are an up direction (U direction, first direction), a right direction (R direction, second direction), a down direction (D direction, third direction), and a left direction (L direction, fourth direction) (see FIG. 4). Of the directions, the first direction (the U direction) and the third direction (the D direction) are opposite directions, and the second direction (the R direction) and the fourth direction (the L direction) are opposite directions.

The flexible tube portion 2c is a tube portion that is provided on a proximal end side of the bending portion 2b and that has flexibility.

The operation section 3 is provided on the proximal end side of the insertion section 2. The operation section 3 is a part that is used by a user of the endoscope 1 to perform various operations. The operation section 3 includes various operation members including a bending lever 3a having a shape of a joystick, the bending lever 3a being for bending the bending portion 2b, for example.

The bending lever 3a is an operation member for bending the bending portion 2b by being tilted in a predetermined direction by receiving an operation force from outside and by pulling each of a plurality of bending operation wires 19 by an appropriate amount.

Figure 1B:
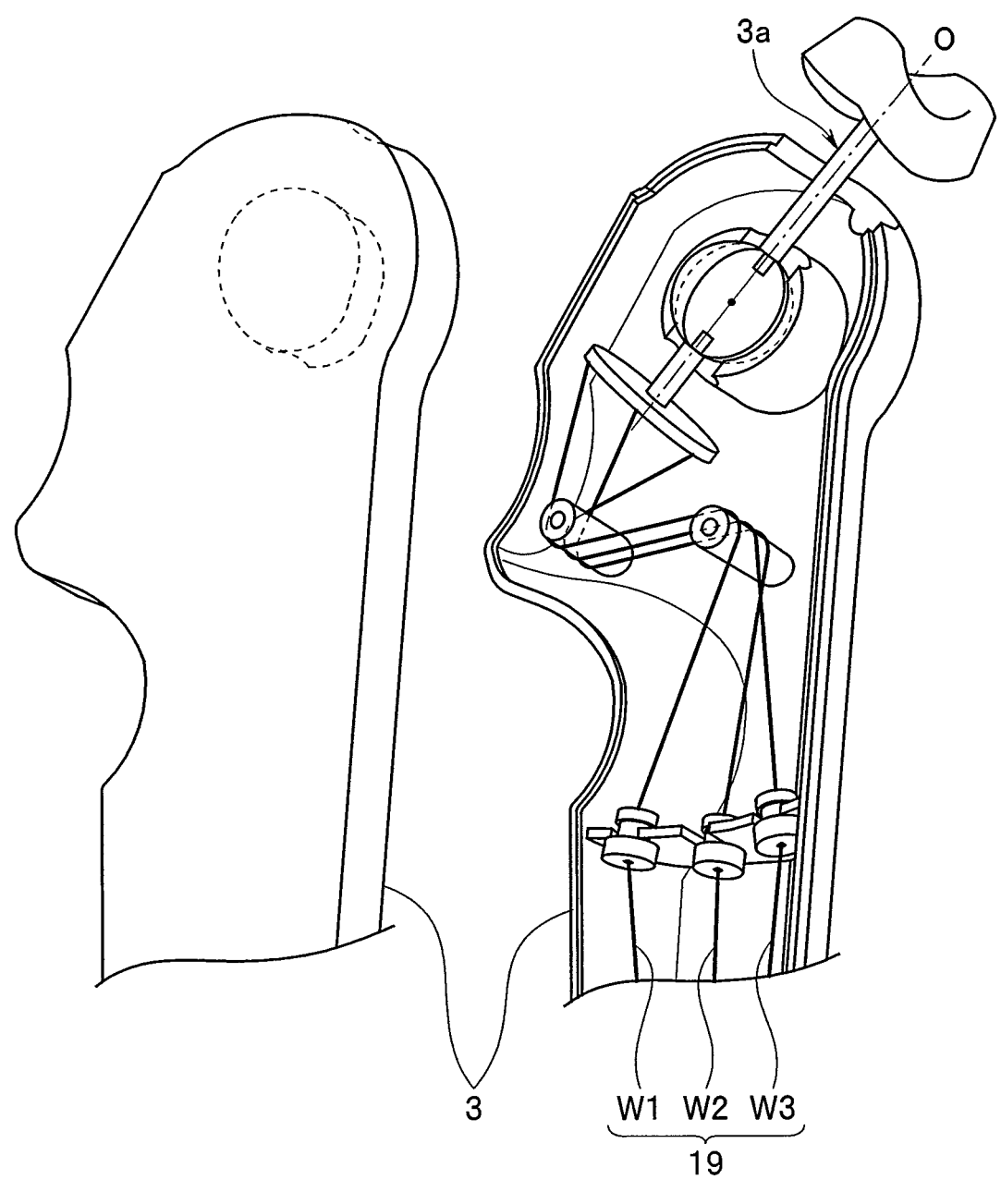
FIG. 1B is a perspective view showing, in an exploded manner, an internal structure of an operation section of the endoscope to which the bending tube of the first embodiment is applied.
Figure 4:
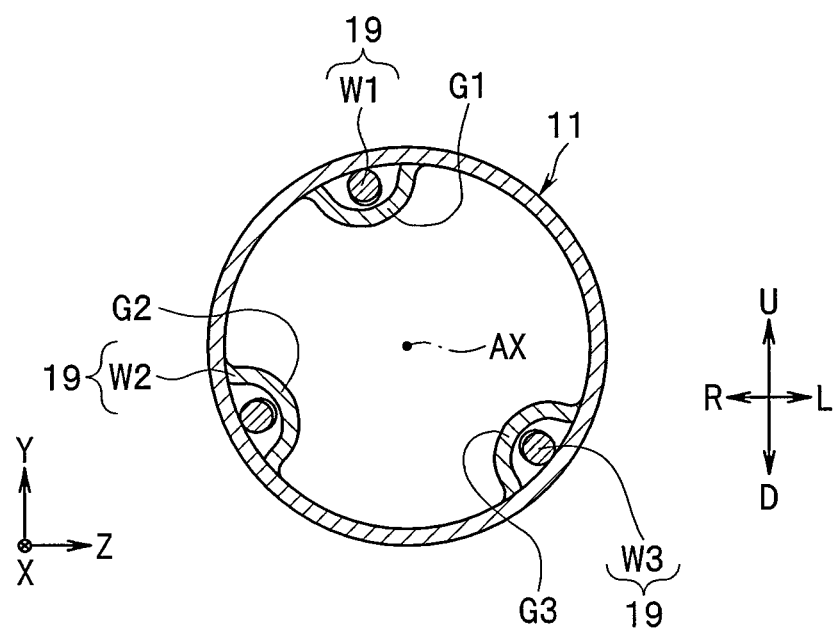
FIG. 4 is a cross-sectional view showing the bending tube unit of the first embodiment from a distal end side toward a proximal end side, the cross-sectional view being perpendicular to a longitudinal axis.

More specifically, as shown in FIGS. 1B, 4, and the like, the bending operation wires 19 include three wires W1, W2, W3. When the bending portion 2b is in a straight state, the bending lever 3a is at a position indicated by a center axis O in FIG. 1B.

The bending lever 3a is an operation member for bending the bending portion 2b in the up direction, the down direction, the left direction, and the right direction by being tilted relative to the center axis O by receiving an operation force from outside and selectively pulling two of the three wires W1, W2, W3. Note that example combinations to be pulled among the three wires W1, W2, W3 will be described later with reference to FIG. 5.

Moreover, a treatment instrument insertion opening 3c is provided in the operation section 3. The treatment instrument insertion opening 3c is a proximal end-side opening of the treatment instrument channel. When a treatment instrument is inserted from the treatment instrument insertion opening 3c, the treatment instrument passes through the treatment instrument channel and protrudes from the distal end-side opening. Various treatments such as removal of stones from the renal pelvis may be performed by the treatment instrument, for example.

The universal cord 4 extends from a side surface of the operation section 3. The light guide, the power cable, the signal cable, and the like are inserted inside the universal cord 4. An extension end of the universal cord 4 is connected to a light source device and a control device. The light guide transmits illumination light supplied from the light source device. The power cable transmits power supplied from the control device. The signal cable transmits control signals outputted from the control device, image pickup signals outputted from the image pickup unit 26, and the like.

Figure 2:
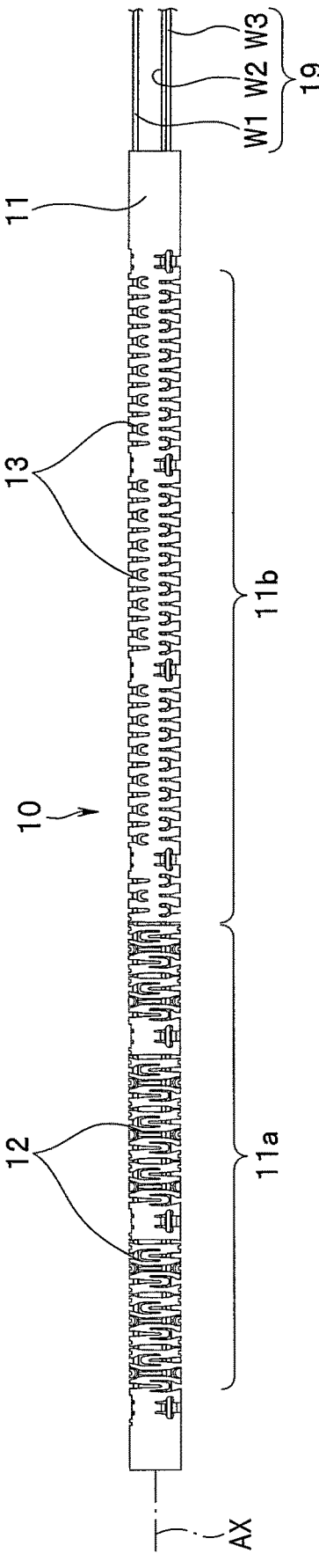
FIG. 2 is a side view showing a configuration of a bending tube unit of the first embodiment.
Figure 3:
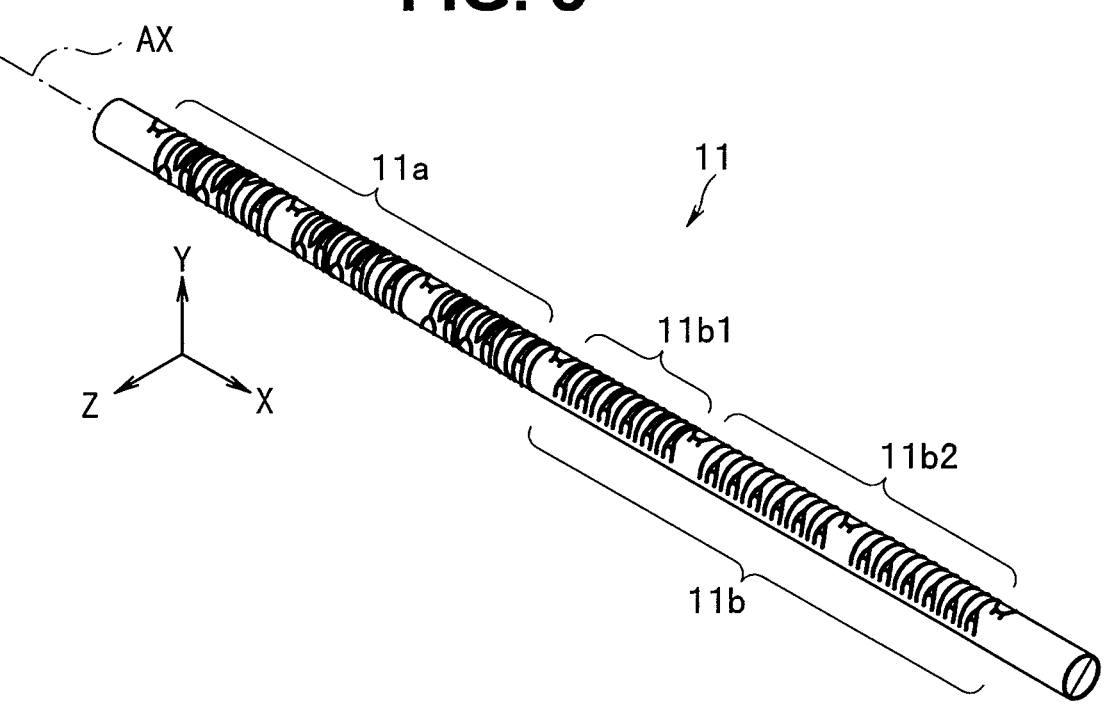
FIG. 3 is a perspective view showing a configuration of the bending tube of the first embodiment.

A bending tube unit 10 is disposed inside the bending portion 2b of the endoscope 1. A structure of the bending tube unit 10 will be described with reference to FIGS. 2 to 4. FIG. 2 is a side view showing the structure of the bending tube unit 10 of the first embodiment. FIG. 3 is a perspective view showing a structure of the bending tube 11 of the first embodiment. FIG. 4 is a cross-sectional view showing the bending tube unit 10 of the first embodiment from a distal end side toward a proximal end side, the cross-sectional view being perpendicular to a longitudinal axis AX.

Note that, in FIGS. 3 and 4, a direction from the distal end side to the proximal end side along the longitudinal axis AX is taken as an X direction (X positive direction), the up (U) direction of up (U)-down (D) bending as a Y direction (Y positive direction), and the left (L) direction of left (L)-right (R) bending as a Z direction (Z positive direction).

As shown in FIG. 2, the bending tube unit 10 includes bending tube 11, and the bending operation wires 19 disposed inside the bending tube 11. A distal end of the bending operation wire 19 is fixed to a distal end side of the bending tube 11 (or a proximal end side of a distal end portion main body provided inside the distal end portion 2a).

The bending tube 11 is a rigid tube having a cylindrical shape (in the present embodiment, a circular cylindrical shape) that is disposed in the bending portion 2b of the endoscope 1 that is an insertion appliance. The longitudinal axis AX is a center axis of the bending tube 11 having a circular cylindrical shape. The bending tube 11 includes a first region 11a on a distal end side in a direction of the longitudinal axis AX, and a second region 11b on a proximal end side in the direction of the longitudinal axis AX. The first region 11a may be taken as an active bending portion, and the second region 11b may be taken as a passive bending portion.

The first region 11a and the second region 11b may have the same or different lengths in the direction of the longitudinal axis AX. The length of the first region 11a in the direction of the longitudinal axis AX, and the length of the second region 11b in the direction of the longitudinal axis AX may be designed as appropriate according to internal components of the endoscope 1, a maximum bending angle, a bending radius, and the like. The second region 11b is provided on a proximal end relative to the first region 11a.

The first region 11a includes a plurality of first slots (slits) 12 that extend in a circumferential direction. The first region 11a is bendable in four directions (the U direction, the R direction, the D direction, the L direction) that are different from each other by 90 degrees in the circumferential direction.

Accordingly, the first slots 12 include four types of first slots 12u, 12r, 12d, 12l (see FIG. 8 described later), center positions CP of which in the circumferential direction are in four directions (the U direction, the R direction, the D direction, the L direction) that are different by 90 degrees in the circumferential direction. Each type of the four types of first slots 12u, 12r, 12d, 12l is provided in plurality in the direction of the longitudinal axis AX. The first region 11a includes first slits 12u, second slits 12r, third slits 12d, and fourth slits 12l. The first, second, third, fourth slits 12u, 12r, 12d, 12l are provided at different positions in the circumferential direction, and at different positions in a longitudinal direction of the bending tube 11. Each of the first, second, third, fourth slits 12u, 12r, 12d, 12l may be provided in plurality. The plurality of first, second, third, fourth slits 12u, 12r, 12d, 12l may be repeatedly provided in the order of the first, second, third, fourth slits in the longitudinal axis direction. The number of repetitions may be three or more. The number of repetitions may be five or more. The number of repetitions may be ten or more. The number of repetitions may be 15 or more. The first, second, third, fourth slits 12u, 12r, 12d, 12l may be provided every 90 degrees in the circumferential direction.

The second region 11b is bendable in two directions (such as the U direction and the D direction) that are different from each other by 180 degrees in the circumferential direction. The second region 11b includes a plurality of second slots (slits) 13 that extend in the circumferential direction.

Accordingly, the second slots 13 include two types of second slots 13u, 13d (see FIG. 9 described later), center positions CP of which in the circumferential direction are in two directions (the U direction, the D direction) that are different by 180 degrees in the circumferential direction. Each type of the two types of second slots 13u, 13d is provided in plurality in the direction of the longitudinal axis AX. The second region 11b includes fifth slits 13u, and sixth slits 13d. The fifth, sixth slits 13u, 13d are provided at different positions in the circumferential direction, and at different positions in the longitudinal direction. In the circumferential direction, the center position CP of the first slit 12u and the center position CP of the fifth slit 13u may be the same. The center position CP of the third slit 12d and the center position CP of the sixth slit 13d may be the same. Each of the fifth, sixth slits 13u, 13d may be provided in plurality. The plurality of fifth, sixth slits 13*u*, 13*d* may be repeatedly provided in the order of the fifth, sixth slits 13*u*, 13*d* in the longitudinal direction. The fifth, sixth slits 13*u*, 13*d* may be provided every 180 degrees in the circumferential direction.

As will be described later with reference to FIG. 7, a range of the first slot 12 in the circumferential direction is greater than a range of the second slot 13 in the circumferential direction. The first, second, third, fourth slits 12*u*, 12*r*, 12*d*, 12*l* extend over a first angle in the circumferential direction, and the fifth, sixth slits 13*u*, 13*d* extend, in the circumferential direction, over a second angle that is smaller than the first angle. Furthermore, the first, second, third, fourth slits 12*u*, 12*r*, 12*d*, 12*l* may be provided over a first length in the circumferential direction, and the fifth, sixth slits 13*u*, 13*d* may be provided over a second length in the circumferential direction, the second length being shorter than the first length.

As shown in FIG. 4 (or FIGS. 8, 9, and the like described later), three bending operation wires 19 are disposed on an inner circumferential side of the bending tube 11 forming a circular cylindrical shape. The three bending operation wires 19 are the wires W1, W2, W3. In the present embodiment, as three long members that are pulled at the time of bending the bending tube 11, the wire W1 that is a first long member, the wire W2 that is a second long member, and the wire W3 that is a third long member are used. However, the long member is not limited to a wire.

Three guiding shape portions G1, G2, G3 are provided on the inner circumferential side of the bending tube 11. The guiding shape portions (guiding surfaces, guides) G1, G2, G3 are provided in the direction of the longitudinal axis AX of the bending tube 11, at different positions in the circumferential direction around the longitudinal axis AX. The guiding surfaces G1, G2, G3 are provided on an inner circumferential surface of the bending tube 11, in the circumferential direction of the bending tube 11. The guiding surfaces are formed such that respective wires 19 (or W1, W2, W3) for bending the bending tube can be slidably attached. In a cross-section perpendicular to the longitudinal axis AX, it suffices if only three wires are attached. The guiding surfaces include a first guiding surface G1, a second guiding surface G2, and a third guiding surface G3. The first, second, third, fourth slits 12*u*, 12*r*, 12*d*, 12*l* include first, second, third, fourth center positions CP, respectively. The first guiding surface G1, the second guiding surface G2, and the third guiding surface G3 are disposed at positions different from the first, second, third, fourth center positions CP.

Three sets are formed by combining two of the three guiding shape portions G1, G2, G3. The three sets that are formed are a set of the guiding shape portion G1 and the guiding shape portion G2, a set of the guiding shape portion G2 and the guiding shape portion G3, and a set of the guiding shape portion G3 and the guiding shape portion G1. An angle formed by two guiding shape portions in the circumferential direction is different among the three sets.

In this manner, the guiding shape portions G1, G2, G3 are disposed in such a way that angles, around the longitudinal axis AX, formed by the guiding shape portion G1 and the guiding shape portion G2, the guiding shape portion G2 and the guiding shape portion G3, and the guiding shape portion G3 and the guiding shape portion G1 are different from one another.

In an example arrangement shown in FIG. 4, the angle formed by the guiding shape portion G3 and the guiding shape portion G1 is the greatest, the angle formed by the guiding shape portion G2 and the guiding shape portion G3 is the second greatest, and the angle formed by the guiding shape portion G1 and the guiding shape portion G2 is the smallest. The guiding surfaces include the first guiding surface G1, the second guiding surface G2, and the third guiding surface G3, and a first distance between the first guiding surface G1 and the second guiding surface G2 is different from a second distance between the first guiding surface G1 and the third guiding surface G3. A distance between the second guiding surface G2 and the third guiding surface G3 may be defined to be a third distance. The first distance may be a distance between a center position of the first guiding shape portion (guide) G1 and a center position of the second guiding shape portion (guide) G2. The second distance may be a distance between the center position of the first guiding shape portion (guide) G1 and a center position of the third guiding shape portion (guide) G3. The third distance may be a distance between the center position of the second guiding shape portion (guide) G2 and the center position of the third guiding shape portion (guide) G3. The first distance, the second distance, and the third distance may be different from one another. The first guiding surface G1, the second guiding surface G2, and the third guiding surface G3 may be disposed at the same position in the longitudinal direction. In a cross-section perpendicular to the longitudinal axis AX, the first guiding surface G1, the second guiding surface G2, and the third guiding surface G3 may be disposed asymmetrically. In the cross-section perpendicular to the longitudinal axis AX, the first guide G1, the second guide G2, and the third guide G3 may form an asymmetrical triangle. The asymmetrical triangle does not have to be a right triangle. In the case where the first guiding surface G1, the second guiding surface G2, and the third guiding surface G3 are disposed at different positions in the longitudinal direction, projections of the first guiding surface G1, the second guiding surface G2, and the third guiding surface G3 on a plane perpendicular to the longitudinal axis AX may be at different positions while being asymmetrical to one another. The projections of the first guide G1 the second guide G2, and the third guide G3 on the plane perpendicular to the longitudinal axis AX may form an asymmetrical triangle. The asymmetrical triangle does not have to be a right triangle.

Furthermore, positions of the guiding shape portion G1, G2, G3 in the circumferential direction around the longitudinal axis AX do not match any of the UDRL directions, and are each at one of between the U direction and the R direction, between the R direction and the D direction, between the D direction and the L direction, and between the L direction and the U direction.

In the example arrangement shown in FIG. 4, the guiding shape portion G1 is disposed between the U direction and the R direction, the guiding shape portion G2 is disposed between the R direction and the D direction, and the guiding shape portion G3 is disposed between the D direction and the L direction. The guiding shape portion G1 is disposed closest to the U direction and somewhat to the R direction. The guiding shape portion G2 is disposed closest to the R direction and somewhat to the D direction. The guiding shape portion G3 is disposed closest to the L direction and closest to the D direction.

The wires W1, W2, W3 that are the three bending operation wires 19 are inserted through the guiding shape portions G1 G2, G3, respectively.

Note that the arrangement of the guiding shape portions G1, G2, G3 and the wires W1, W2, W3 shown in FIG. 4 is an example. Accordingly, the arrangement of the guiding shape portions G1, G2, G3 and the wires W1, W2, W3 may be optimized according to arrangement of each member inserted in the insertion section 2, such as the power cable, the signal cable, the light guide, the bending operation wire 19, and the treatment instrument channel. In relation to the arrangement, it suffices if conditions are met, the conditions being that the guiding shape portions G1, G2, G3 and the wires W1, W2, W3 do not match any of the UDRL directions and that gaps between angles around the longitudinal axis AX are different.

At the time of bending the first region 11a in one of the four directions (the U direction, the R direction, the D direction, the L direction), two of the wires W1, W2, W3 are pulled.

Figures 5, 6:
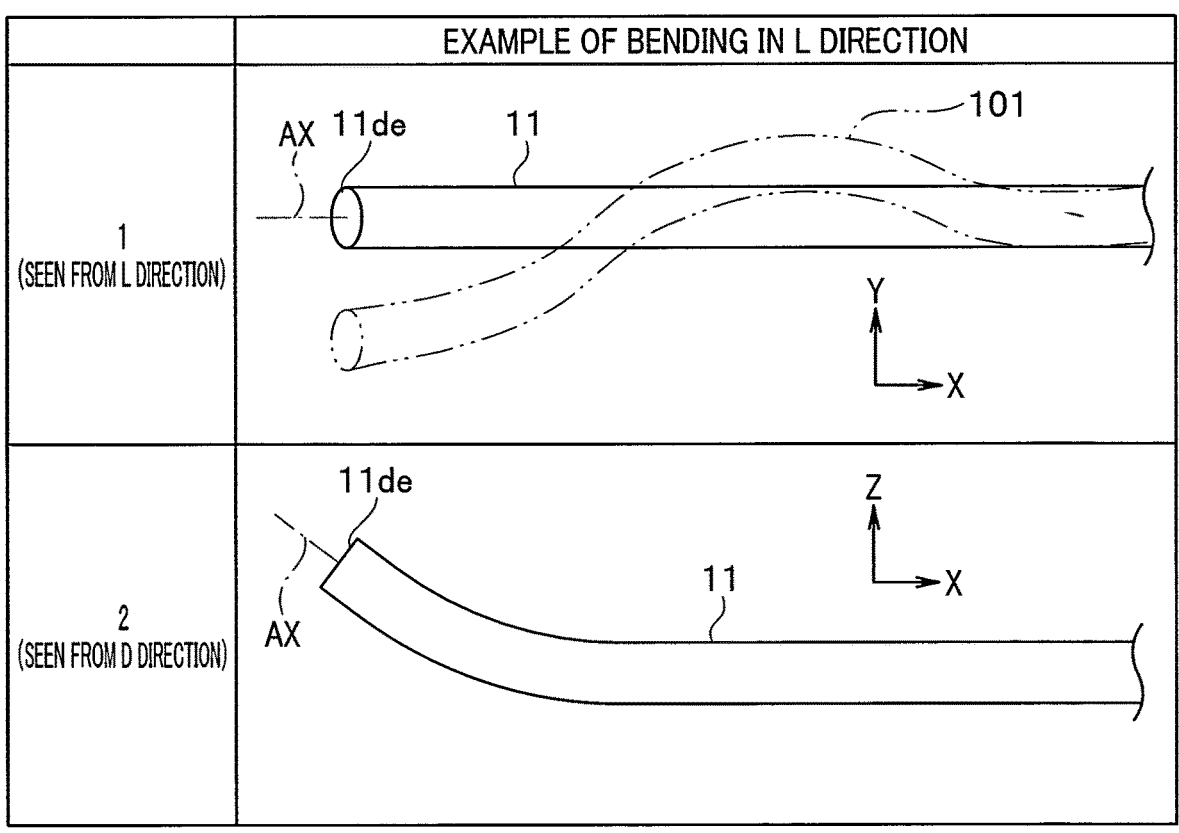
FIG. 5 is a table showing, in relation to an example arrangement of the first embodiment shown in FIG. 4, which of three wires are to be pulled in combination when bending a first region of the bending tube in one of UDRL directions.
FIG. 6 is a table showing an example of a bent shape when the bending tube of the first embodiment is bent in an L direction.

FIG. 5 is a table showing, in relation to the example arrangement of the first embodiment shown in FIG. 4, which of the three wires W1, W2, W3 are to be pulled in combination when bending the first region 11a of the bending tube 11 in one of the UDRL directions.

More specifically, at the time of bending the first region 11a (and thus, the bending portion 2b; the same applies hereinafter) in the U direction (the first direction), the wire W1 disposed closest to the U direction is pulled. However, because the wire W1 is disposed somewhat to the R direction, if only the wire W1 is pulled, the first region 11a is bent somewhat to the R direction. Accordingly, the wire W3 that is closest to the L direction is pulled, and correction is performed such that the first region 11a is not bent in the R direction. In this manner, at the time of bending the first region 11a in the U direction, the wire W1 is mainly pulled, and the wire W3 is pulled for correction. In other words, a first amount of pull on the wire W1 is greater than a third amount of pull on the wire W3.

At the time of bending the first region 11a in the R direction (the second direction), the wire W2 disposed closest to the R direction is pulled. However, because the wire W2 is disposed somewhat to the D direction, if only the wire W2 is pulled, the first region 11a is bent somewhat to the D direction. Accordingly, the wire W1 that is closest to the U direction is pulled, and correction is performed such that the first region 11a is not bent in the D direction. In this manner, at the time of bending the first region 11a in the R direction, the wire W2 is mainly pulled, and the wire W1 is pulled for correction. In other words, a second amount of pull on the wire W2 is greater than a first amount of pull on the wire W1.

At the time of bending the first region 11a in the D direction (the third direction), the wire W3 disposed closest to the D direction is pulled. However, because the wire W3 is disposed also close to the L direction, if only the wire W3 is pulled, the first region 11a is bent also to the L direction. Accordingly, the wire W2 that is closest to the R direction is pulled, and correction is performed such that the first region 11a is not bent in the L direction. In this manner, at the time of bending the first region 11a in the D direction, the wire W3 is mainly pulled, and the wire W2 is pulled for correction. In other words, a third amount of pull on the wire W3 is greater than a second amount of pull on the wire W2.

At the time of bending the first region 11a in the L direction (the fourth direction), the wire W3 disposed closest to the L direction is pulled. However, because the wire W3 is disposed also close to the D direction, if only the wire W3 is pulled, the first region 11a is bent also to the D direction. Accordingly, the wire W1 that is closest to the U direction is pulled, and correction is performed such that the first region 11a is not bent in the D direction. In this manner, at the time of bending the first region 11a in the L direction, the wire W3 is mainly pulled, and the wire W1 is pulled for correction. In other words, a third amount of pull on the wire W3 is greater than a first amount of pull on the wire W1.

Note that the wires to be pulled are W1 and W3 for both cases of bending the first region 11a in the U direction and bending the first region 11a in the L direction. However, there is a difference between main use and use for correction as described above, and a ratio of the third amount of pull on the wire W3 to the first amount of pull on the wire W1 is different between the two cases. (1) At the time of bending the first region 11a in the first direction, the first wire W1 is pulled by the first amount of pull, and the third wire W3 is pulled by the second amount of pull. (2) At the time of bending the first region 11a in the second direction, the first wire W1 and the second wire W2 are pulled. (3) At the time of bending the first region 11a in the third direction, the second long member and the third long member are pulled. (4) At the time of bending the first region 11a in the fourth direction, the first wire W1 is pulled by the third amount of pull, and the third wire W3 is pulled by a fourth amount of pull. A ratio between the first amount of pull and the second amount of pull is different from a ratio between the third amount of pull and the fourth amount of pull.

More specifically, when the first amount of pull is given as WX1 and the third amount of pull is given as WX3, the wire W1 is for main use and the wire W3 is used for correction in relation to bending in the U direction, and thus, WX1>WX3 is established. Furthermore, in relation to bending in the L direction, the wire W3 is for main use, and the wire W1 is used for correction, and thus, WX3>WX1 is established. Accordingly, the ratio between the amounts of pull (WX3/WX1) is greater at the time of bending in the L direction than at the time of bending in the U direction.

FIG. 6 is a table showing an example of a bent shape when the bending tube 11 of the first embodiment is bent in the L direction.

Section 1 in FIG. 6 shows the bending tube 11 that is bent in the L direction and that is seen from the L direction. When seen from the L direction, the bending tube 11 is bent in neither the U direction (the Y positive direction) nor the D direction (Y negative direction), and a distal end 11de faces the L direction.

Section 2 in FIG. 6 shows the bending tube 11 that is bent in the L direction and that is seen from the D direction. When seen from the D direction, the bending tube 11 is bent in the L direction (the Z positive direction), and the distal end 11de faces the L direction.

In section 1 in FIG. 6, a state where a conventional bending tube 101 is unintentionally bent is shown by a dash-dot-dotted line, the bending tube 101 including, on a distal end side, a first region for being bent in four directions (the U direction, the R direction, the D direction, the L direction), and including, on a proximal end side, a second region for being bent in two directions (the U direction, the D direction).

When a bending operation wire is pulled to bend the conventional bending tube 101 in the L direction, a pull force is applied also to the second region even when attempting to bend the first region in the L direction, and bending in the U direction and the D direction is unintentionally caused.

A structure of the bending tube 11 of the present embodiment for preventing such unintentional bending of the conventional bending tube 101 will be described with reference to FIG. 7. FIG. 7 is a diagram showing, in relation to the bending tube 11 of the first embodiment, structures of the first slots 12u, 12d in the first region 11a, structures of the second slots 13*u*, 13*d* in a first partial region (second region) 11*b*1 in the second region 11*b*, and structures of the second slots 13*u*, 13*d* in a second partial region (third region) 11*b*2 in the second region 11*b*. Note that, in FIG. 7, illustration of the first slots 12*r*, 12*l* in the first region 11*a* is omitted, and the first slots 12*r*, 12*l* are shown in FIG. 8 described later. There may be provided the third region 11*b*2 that is provided on a proximal end relative to the second region 11*b*1. The third region 11*b*2 includes a seventh slit 13*u*, and an eighth slit 13*d*. The seventh, eighth slits 13*u*, 13*d* are provided at different positions in the circumferential direction, and at different positions in the longitudinal direction. The seventh, eighth slits 13*u*, 13*d* are provided over a third angle in the circumferential direction. The second angle is greater than the third angle.

Figure 7:
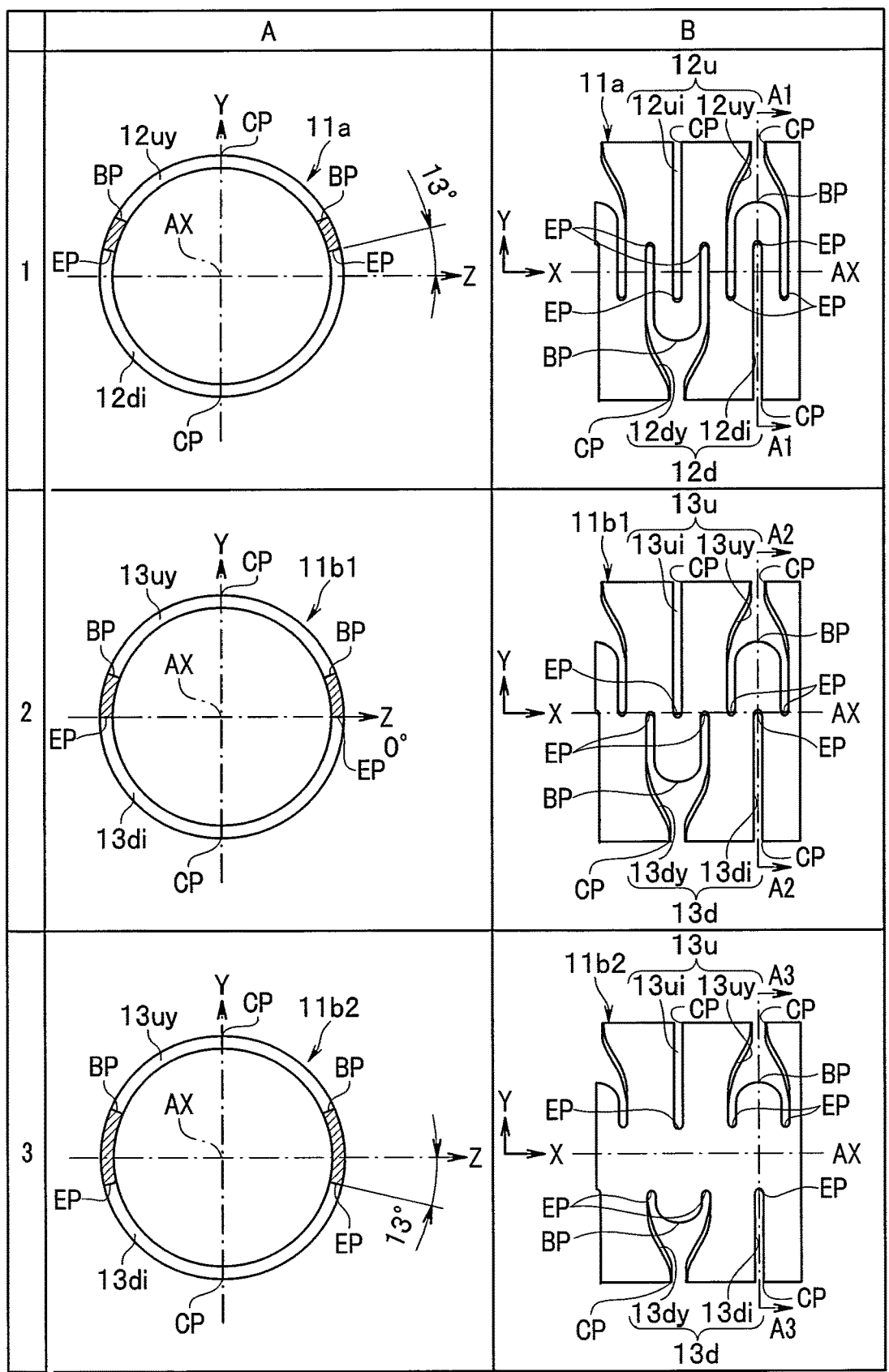
FIG. 7 is a diagram showing, in relation to the bending tube of the first embodiment, a structure of a slot in the first region, a structure of a slot in a first partial region in a second region, and a structure of a slot in a second partial region in the second region.
Figure 8:
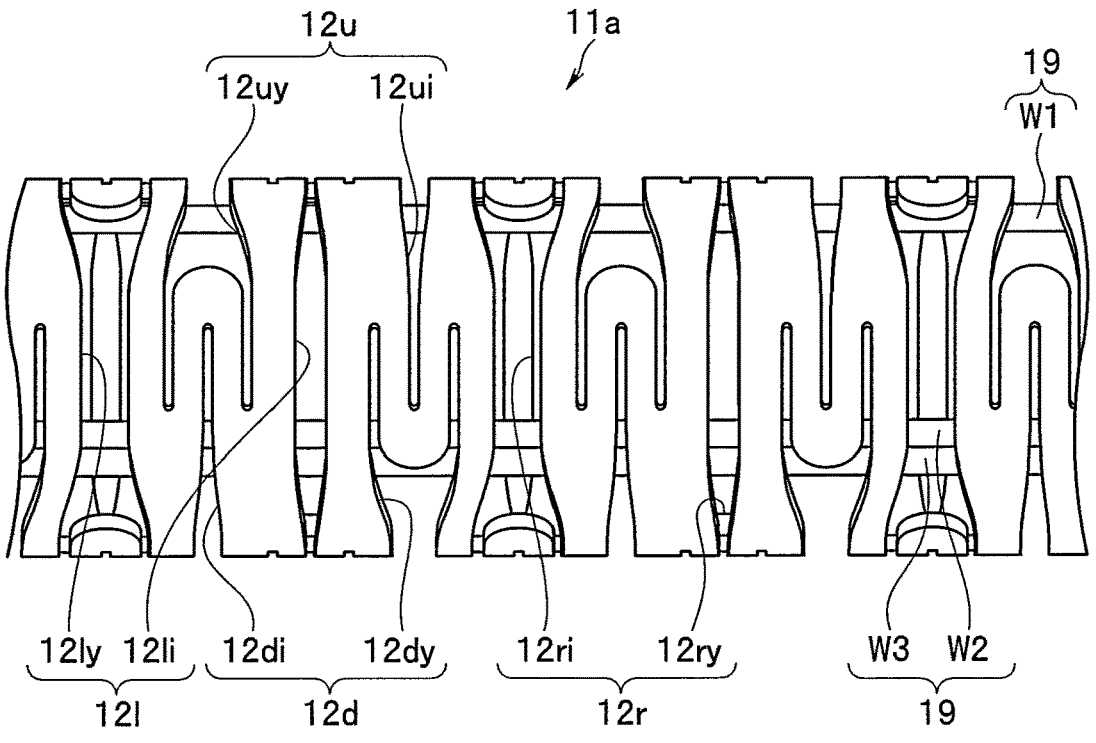
FIG. 8 is a side view showing structures of first slots in the first region of the bending tube of the first embodiment.

Section 1A in FIG. 7 shows a cross-section of the first slots 12*u*, 12*d* provided in the first region 11*a* of the bending tube 11, the cross-section being perpendicular to the longitudinal axis AX (a cross-sectional view taken along A1-A1 in section 1B in FIG. 7). Section 1B in FIG. 7 shows a side view of the first slots 12*u*, 12*d* provided in the first region 11*a*.

Section 2A in FIG. 7 shows a cross-section of the second slots 13*u*, 13*d* provided in the first partial region 11*b*1 in the second region 11*b* of the bending tube 11, the cross-section being perpendicular to the longitudinal axis AX (a cross-sectional view taken along A2-A2 in section 2B in FIG. 7). Section 2B in FIG. 7 shows a side view of the second slots 13*u*, 13*d* provided in the first partial region 11*b*1.

Section 3A in FIG. 7 shows a cross-section of the second slots 13*u*, 13*d* provided in the second partial region 11*b*2 in the second region 11*b* of the bending tube 11, the cross-section being perpendicular to the longitudinal axis AX (a cross-sectional view taken along A3-A3 in section 3B in FIG. 7). Section 3B in FIG. 7 shows a side view of the second slots 13*u*, 13*d* provided in the second partial region 11*b*2.

Each of sections 1A, 2A, 3A in FIG. 7 shows a YZ coordinate where an X-axis of an XYZ coordinate system matches the longitudinal axis AX. As described above, the Y positive direction is the U direction, the Y negative direction is the D direction, a Z negative direction is the R direction, and the Z positive direction is the L direction.

With the bending tube 11 of the present embodiment, the range of the first slot 12 in the circumferential direction is greater than 180 degrees, and the range of the second slot 13 in the circumferential direction is 180 degrees or less. Accordingly, the first region 11*a* where the first slot 12 is provided can be easily bent, and the second region 11*b* where the second slot 13 is provided is harder to bend than the first region 11*a*. Therefore, even when the first region 11*a* is bent in the R direction or the L direction, the second slot 13 is not bent in the U direction or the D direction, and unintentional bending as in the case of the conventional bending tube 101 may be prevented.

For example, the range of the first slot 12 in the circumferential direction is 206 degrees or more. Section 1 in FIG. 7 shows an example where the range of the first slot 12 in the circumferential direction is 206 degrees.

The first slot 12*u* is the first slot 12, the center position CP of which in the circumferential direction is in the U direction (thereby intersecting with a positive part on a Y-axis). The first slot 12*u* includes a branched slot (branched portion) 12*uy* and a linear slot 12*ui*. Ranges of the branched slot 12*uy* and the linear slot 12*ui* in the circumferential direction are both 206 degrees. At least one first, second, third, fourth slit 12*u*, 12*r*, 12*d*, 12*l*, the fifth, sixth slit 13*u*, 13*d* may include a first branched portion (12*uy*, 12*ry*, 12*ly*, 12*dy*, 13*uy*, 13*dy*). At least one first, second, third, fourth slit 12*u*, 12*r*, 12*d*, 12*l*, the fifth, sixth slit 13*u*, 13*d* may include a second branched portion (12*uy*, 12*ry*, 12*ly*, 12*dy*, 13*uy*, 13*dy*).

One side of the branched slot 12*uy* in the circumferential direction is branched at a branching point BP to reach end parts EP. Furthermore, the other side of the branched slot 12*uy* of the present embodiment in the circumferential direction is branched from a branching point BP to reach end parts EP. In other words, both sides of the branched slot 12*uy* in the circumferential direction are branched.

In a plan view obtained by cutting the bending tube 11 along a plane parallel to the longitudinal axis AX and spreading a circular cylindrical surface, branched parts near the branching points BP of the branched slots 12*uy*, 12*dy* (and the branched slots 12*ry*, 12*ly* shown in FIG. 8) each form a curved line.

The linear slot (seventh slit) 12*ui* is a slot extending along a plane perpendicular to the longitudinal axis AX. Accordingly, in the plan view obtained by cutting the bending tube 11 along a plane parallel to the longitudinal axis AX and spreading the circular cylindrical surface, the linear slot 12*ui* has a linear shape that is orthogonal to the longitudinal axis AX. At least one of the first region 11*a* or the second region 11*b* may further include the linear-shaped seventh slit. At least one of the first slit 12*u* or the fifth slit 13*u* may be provided at the same position as seventh slit 12*ui*, 13*ui* in the longitudinal direction.

The first slot 12*d* is the first slot 12, the center position CP of which in the circumferential direction is in the D direction (thereby intersecting with a negative part on the Y-axis). The first slot 12*d* includes a branched slot 12*dy* and a linear slot (seventh slit) 12*di*. Ranges of the branched slot 12*dy* and the linear slot 12*di* in the circumferential direction are both 206 degrees. At least one of the first slit 12*d* or the sixth slit 13*d* may be provided at the same position as seventh slit 12*di*, 13*di* in the longitudinal direction.

One side of the branched slot 12*dy* in the circumferential direction is branched at a branching point BP to reach end parts EP. Furthermore, the other side of the branched slot 12*dy* of the present embodiment in the circumferential direction is branched from a branching point BP to reach end parts EP. In other words, both sides of the branched slot 12*dy* in the circumferential direction are branched (however, it suffices if only one side is branched).

The linear slot 12*di* is a slot extending along a plane perpendicular to the longitudinal axis AX. Accordingly, in the plan view obtained by cutting the bending tube 11 along a plane parallel to the longitudinal axis AX and spreading the circular cylindrical surface, the linear slot 12*di* has a linear shape that is orthogonal to the longitudinal axis AX.

With respect to the first slot 12*u* and the first slot 12*d*, there is a pair that is provided at the same position in the direction of the longitudinal axis AX. Furthermore, at least one of the pair is a branched slot.

With respect to a pair of the branched slot 12*uy* and the linear slot 12*di*, center positions CP in the circumferential direction (or more accurately, center positions of widths in the longitudinal axis AX direction at the center positions CP in the circumferential direction; the same applies hereinafter) are provided at the same positions in the direction of the longitudinal axis AX. Accordingly, when the ranges of the first slot 12*u* and the first slot 12*d* in the circumferential direction are made greater than 180 degrees, the two slots are prevented from being coupled into one, and the bending tube 11 may be prevented from being separated into two.

For the same reason, also with respect to each of a pair of the branched slot 12*dy* and the linear slot 12*ui*, a pair of the branched slot 12*ry* and a linear slot 12*li*, and a pair of the branched slot 12*ly* and a linear slot 12*ri* described later, at least one of the pair is made a branched slot. The fourth slit 12*l* may be provided at the same position as the seventh slit 12*li* in the longitudinal direction. The second slit 12*r* may be provided at the same position as the seventh slit 12*ri* in the longitudinal direction.

The pair of the branched slot 12*uy* and the linear slot 12*di* mainly functions at the time of bending of the bending tube 11 in the U direction. More specifically, the bending tube 11 is bent in the U direction due to a width, in the direction of the longitudinal axis AX, at the center position CP of the branched slot 12*uy* being reduced and a width, in the direction of the longitudinal axis AX, at the center position CP of the linear slot 12*di* being increased.

With respect to the pair of the branched slot 12*dy* and the linear slot 12*ui*, center positions CP in the circumferential direction are provided at the same positions in the direction of the longitudinal axis AX. The pair of the branched slot 12*dy* and the linear slot 12*ui* mainly functions at the time of bending of the bending tube 11 in the D direction. More specifically, the bending tube 11 is bent in the D direction due to a width, in the direction of the longitudinal axis AX, at the center position CP of the branched slot 12*dy* being reduced and a width, in the direction of the longitudinal axis AX, at the center position CP of the linear slot 12*ui* being increased.

Section 2 in FIG. 7 shows an example where the range, in the circumferential direction, of the second slot 13 provided in the first partial region 11*b*1 is made 180 degrees. As shown in FIG. 3, the first partial region 11*b*1 is provided on the distal end side of the second region 11*b* in the direction of the longitudinal axis AX.

The second slot 13*u* is the second slot 13, the center position CP of which in the circumferential direction is in the U direction (thereby intersecting with a positive part on the Y-axis). The second slot 13*u* includes the branched slot 13*uy* and the linear slot (seventh slit) 13*ui*. Structures of the branched slot 13*uy* and the linear slot 13*ui* are the same as the structures of the branched slot 12*uy* and the linear slot 12*ui*, except that the ranges in the circumferential direction are 180 degrees.

The second slot 13*d* is the second slot 13, the center position CP of which in the circumferential direction is in the D direction (thereby intersecting with a negative part on the Y-axis). The second slot 13*d* includes the branched slot 13*dy* and the linear slot (seventh slit) 13*di*. Structures of the branched slot 13*dy* and the linear slot 13*di* are the same as the structures of the branched slot 12*dy* and the linear slot 12*di*, except that the ranges in the circumferential direction are 180 degrees.

Section 3 in FIG. 7 shows an example where the range, in the circumferential direction, of the second slot 13 provided in the second partial region 11*b*2 is less than 180 degrees. As shown in FIG. 3, the second partial region 11*b*2 is provided on the proximal end side of the second region 11*b* in the direction of the longitudinal axis AX.

Structures of the branched slots 13*uy*, 13*dy* and the linear slots 13*ui*, 13*di* in the second partial region 11*b*2 are the same as the structures of the branched slots 13*uy*, 13*dy* and the linear slots 13*ui*, 13*di* in the first partial region 11*b*1, except that the ranges in the circumferential direction are less than 180 degrees.

In the example shown in section 3 in FIG. 7, the ranges of the branched slots 13*uy*, 13*dy* and the linear slots 13*ui*,

13*di* in the circumferential direction are 154 degrees. In this manner, the range, in the circumferential direction, of the second slot 13 in the second partial region 11*b*2 may be made 154 degrees or less.

Note that, in the example shown in FIG. 7, the range, in the circumferential direction, of the second slot 13 in the first partial region 11*b*1 on the distal end side is made 180 degrees, and the range, in the circumferential direction, of the second slot 13 in the second partial region 11*b*2 on the proximal end side is made less than 180 degrees, but such an example is not restrictive.

For example, a plurality of second slots 13, the range of which in the circumferential direction is 180 degrees, and a plurality of second slots 13, the range of which in the circumferential direction is less than 180 degrees, may be alternately provided in the direction of the longitudinal axis AX. Furthermore, it is not necessary to provide both the first partial region 11*b*1 and the second partial region 11*b*2 in the second region 11*b*, and it is also possible to provide one of the first partial region 11*b*1 and the second partial region 11*b*2. The range of the second slot 13 in the circumferential direction may be set to any range on condition that the range of the first slot 12 in the circumferential direction is greater than the range of the second slot 13 in the circumferential direction.

FIG. 8 is a side view showing structures of the first slots 12 in the first region 11*a* of the bending tube 11 of the first embodiment.

As described above, four types of first slots 12*u*, 12*r*, 12*d*, 12*l*, the center positions CP of which in the circumferential direction are in the U direction, the R direction, the D direction, and the L direction, respectively, are provided in plurality in the first region 11*a*.

Like the first slots 12*d*, 12*u* described above, the first slots 12*r*, 12*l* include respective branched slots 12*ry*, 12*ly* and respective linear slots 12*ri*, 12*li*. The range in the circumferential direction is 206 degrees for each of the branched slots 12*ry*, 12*ly* and the linear slots 12*ri*, 12*li*, for example.

Both sides (or one side) of the branched slot 12*ry*, 12*ly* in the circumferential direction is branched at the branching point BP to reach the end parts EP. In the plan view obtained by cutting the bending tube 11 along a plane parallel to the longitudinal axis AX and spreading the circular cylindrical surface, the linear slot 12*ri*, 12*li* has a linear shape that is orthogonal to the longitudinal axis AX.

A pair of the branched slot 12*ry* and the linear slot 12*li* have the center positions CP in the circumferential direction provided at the same positions in the direction of the longitudinal axis AX. The pair of the branched slot 12*ry* and the linear slot 12*li* mainly functions at the time of bending of the bending tube 11 in the R direction. More specifically, the bending tube 11 is bent in the R direction due to a width, in the direction of the longitudinal axis AX, at the center position CP of the branched slot 12*ry* being reduced and a width, in the direction of the longitudinal axis AX, at the center position CP of the linear slot 12*li* being increased.

A pair of the branched slot 12*ly* and the linear slot 12*ri* have the center positions CP in the circumferential direction provided at the same positions in the direction of the longitudinal axis AX. The pair of the branched slot 12*ly* and the linear slot 12*ri* mainly functions at the time of bending of the bending tube 11 in the L direction. More specifically, the bending tube 11 is bent in the L direction due to a width, in the direction of the longitudinal axis AX, at the center position CP of the branched slot 12*ly* being reduced and a width, in the direction of the longitudinal axis AX, at the center position CP of the linear slot 12*ri* being increased.

Note that the range of the first slot 12 in the circumferential direction may be set to any range on condition that the range of the first slot 12 in the circumferential direction is greater than the range of the second slot 13 in the circumferential direction.

For example, the range in the circumferential direction does not have to be the same for all of the four types of first slots 12*u*, 12*r*, 12*d*, 12*l*, and the range of the first slots 12*u*, 12*d* in the circumferential direction and the range of the first slots 12*r*, 12*l* in the circumferential direction may be made different. When considering that the second slots 13 include only slots for bending in the UD directions, a maximum bending angle in the UD direction may be made 270 degrees, for example, and a maximum bending angle in the RL direction may be made about 90 degrees, for example.

Figure 9:
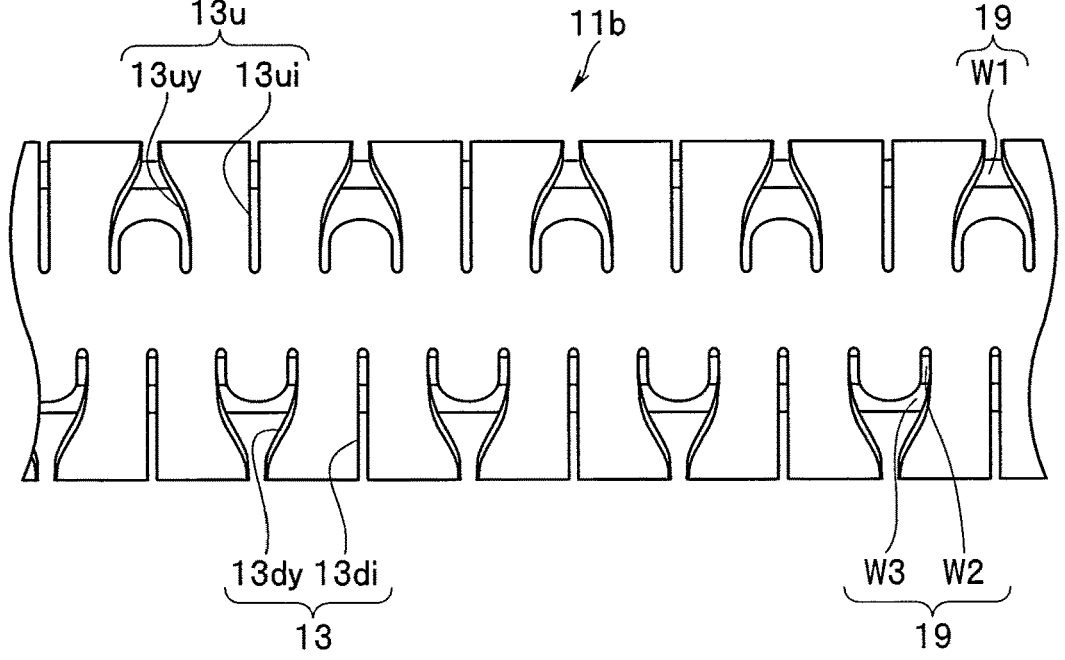
FIG. 9 is a side view showing structures of second slots in the second region of the bending tube of the first embodiment.

FIG. 9 is a side view showing structures of the second slots 13 in the second region 11*b* of the bending tube 11 of the first embodiment.

As described above, two types of second slots 13*u*, 13*d*, the center positions CP of which in the circumferential direction are in the U direction and the D direction, respectively, are provided in plurality in the second region 11*b*.

The center positions CP of the two types of second slots 13*u*, 13*d* in the circumferential direction are the same, respectively, as the center positions of the two types of first slots 12*u*, 12*d* among the four types of first slots 12*u*, 12*r*, 12*d*, 12*l*.

As can be seen when comparing FIG. 8 and FIG. 9, an area of any one first slot 12 is greater than an area of any one second slot 13. In other words, an area of a second slot 13 having a greatest area among the plurality of types of second slots 13 is smaller than an area of a first slot 12 having a smallest area among the plurality of types of first slots 12. Areas of the first, second, third, fourth slits 12*u*, 12*r*, 12*d*, 12*l* are greater than areas of the fifth, sixth slits 13*u*, 13*d*.

Note that an example is described above where the first slot 12 and the second slot 13 both include a branched slot, but such an example is not restrictive, and one of the first slot 12 and the second slot 13 may include the branched slot, or the first slot 12 and the second slot 13 do not have to include the branched slot. For example, the first slot 12 and the second slot 13 may each be formed from only the linear slot.

Figure 10:
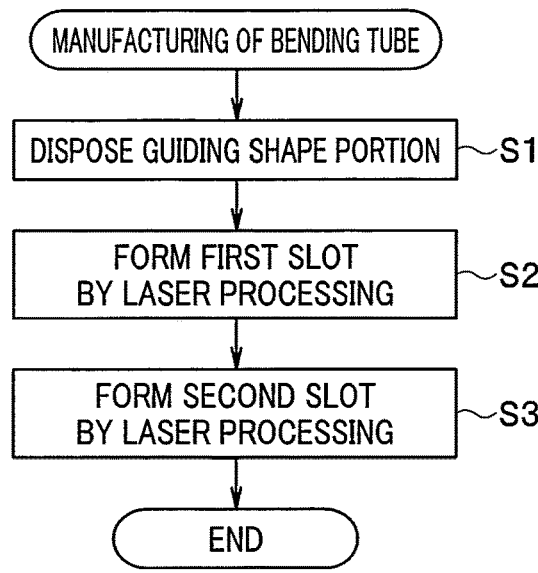
FIG. 10 is a flowchart showing an example of a manufacturing method of the bending tube of the first embodiment.

FIG. 10 is a flowchart showing an example of a manufacturing method of the bending tube 11 of the first embodiment.

The bending tube 11 is formed by forming, by laser processing or the like, a plurality of slots in a metal pipe having a circular cylindrical shape. At the time of laser processing, a laser irradiation position is fixed, and the slot is formed by rotating the metal pipe, for example. Alternatively, the slot may also be formed by fixing the metal pipe and causing laser to penetrate through a front side and a rear side of the metal pipe present in a laser irradiation direction while changing the laser irradiation position.

One slot is a long hole extending in the circumferential direction, and is provided in a range of less than 360 degrees around the longitudinal axis AX of the bending tube 11 (this is because if the range reaches 360 degrees in the circumferential direction, the metal pipe as material is cut in two).

When the process shown in FIG. 10 is started, the three guiding shape portions G1, G2, G3 are provided on an inner circumferential side of the bending tube 11 (step S1). The guiding shape portions G1, G2, G3 may be formed by bending the metal pipe as the material of the bending tube 11 radially inward at a plurality of positions along the longitudinal axis AX. Alternatively, the guiding shape portions G1, G2, G3 may each be provided by fixing another member on the inner circumferential side of the bending tube 11.

The first slot 12 that extends in the circumferential direction is formed in the first region 11*a* on the distal end side in the direction of the longitudinal axis AX (step S2). Here, each of the four types of first slots 12*u*, 12*r*, 12*d*, 12*l* is provided in plurality in the direction of the longitudinal axis AX, the four types of first slots 12*u*, 12*r*, 12*d*, 12*l* being in four directions (the U direction, the R direction, the D direction, the L direction) the center positions CP in the circumferential direction of which are different from each other by 90 degrees in the circumferential direction.

The second slot 13 that extends in the circumferential direction is formed in the second region 11*b* on the proximal end side in the direction of the longitudinal axis AX (step S3). Here, each of the two types of second slots 13*u*, 13*d* is provided in plurality in the direction of the longitudinal axis AX, the two types of second slots 13*u*, 13*d* being in two directions (the U direction, the D direction) the center positions CP in the circumferential direction of which are different from each other by 180 degrees in the circumferential direction.

As described above, the first slot 12 and the second slot 13 are provided in such a way that the range of the first slot 12 in the circumferential direction is greater than the range of the second slot 13 in the circumferential direction.

By forming the first slot 12 and the second slot 13 in one metal pipe by laser processing, the bending tube 11 that integrally includes the first region 11*a* and the second region 11*b* is formed. Accordingly, in the case of using the first region 11*a* as an active bending portion and the second region 11*b* as a passive bending portion, for example, a task of joining, using a joint, an active bending portion and a passive bending portion that are formed as separate bodies may be omitted.

The bending tube 11 is manufactured by performing the process in step S3 in the above manner.

Note that FIG. 10 shows an example of the manufacturing method, and the order of processes shown in FIG. 10 is not restrictive. For example, the process in step S1, the process in step S2, and the process in step S3 may be performed in any order, or any two or more processes may be performed in parallel. The manufacturing method of the bending tube 11 of the insertion appliance may include a step of providing, in the circumferential direction of the bending tube 11, the first, second, third guiding surfaces G1, G2, G3 on the inner circumferential surface of the bending tube 11, a step of providing the first, second, third, fourth slits 12*u*, 12*r*, 12*d*, 12*l* in the first region 11*a* of the bending tube 11 in the longitudinal direction of the bending tube 11, at different positions in the circumferential direction, and a step of providing the fifth, sixth slits 13*u*, 13*d* in the second region 11*b* in the longitudinal direction, at different positions in the circumferential direction. Here, the first, second, third, fourth slits 12*u*, 12*r*, 12*d*, 12*l* are provided over the first angle in the circumferential direction, and the fifth, sixth slits 13*u*, 13*d* are provided over the second angle smaller than the first angle in the circumferential direction.

When the bending tube 11 is manufactured, the wires W1 W2, W3 are inserted through the three guiding shape portions G1, G2, G3, respectively. The bending tube unit 10 is formed by fixing each of distal ends of the wires W1, W2, W3 to the distal end side of the bending tube 11, for example.

With the bending tube 11 of the first embodiment, bending in the four directions is performed using the wires W1, W2, W3 that are three long members, and thus, a diameter of the insertion section 2 of the endoscope 1 can be reduced and insertability can be increased compared with a general structure that uses four wires.

Bendability of the first region 11a and bendability of the second region 11b are appropriately set by making the range of the first slot 12 in the circumferential direction greater than 180 degrees and the range of the second slot 13 in the circumferential direction 180 degrees or less. In other words, the first region 11a is easily bent, and the second region 11b is harder to bend than the first region 11a. Accordingly, even when the first region 11a is bent in the R direction or the L direction using the three wires W1, W2, W3, the second region 11b can be prevented from being bent unintentionally in the U direction or the D direction. In other words, control can be performed to achieve a desired bent shape when bending operation is performed using the three wires W1, W2, W3. The first angle may be greater than 180 degrees, and the second angle may be 180 degrees or less.

Furthermore, because the second region 11b on the proximal end side of the bending tube 11 is structured to be bent in two directions instead of four directions, a length of the entire bending tube 11 can be reduced.

Furthermore, compared with using a structure where a plurality of bending pieces are swingably coupled, using the bending tube 11 that is formed by performing laser processing on one metal pipe allows manufacturing cost to be reduced, and also, a structure that is suitable for a single-use endoscope can be achieved.

RELATED ART

Now, a sensor that measures physical quantity that is applied to a subject is sometimes provided inside the distal end portion 2a of the endoscope 1. The sensor measures physical quantity such as pressure, temperature, or the like. To prevent breaking, the sensor is disposed in a space inside the distal end portion 2a where the sensor does not protrude from a circular cylindrical surface of the distal end portion 2a. In this case, to allow the sensor to accurately measure the physical quantity that is applied to the subject, the space where the sensor is disposed is made to communicate with outside of the endoscope 1, or in other words, inside of the subject.

However, when the distal end portion 2a of the endoscope 1 comes into contact with tissue of the subject, such as a mucus membrane, or impurities are attached to the distal end portion 2a, for example, the space where the sensor is disposed may become a closed space and the physical quantity may not be accurately measured. Accordingly, related art that enables the sensor to more accurately measure the physical quantity will be described.

Note that, in relation to the related art, parts the same as parts in the first embodiment described above will be denoted by the same reference sign, and description will be omitted as appropriate.

First Example of Related Art

Figure 11:
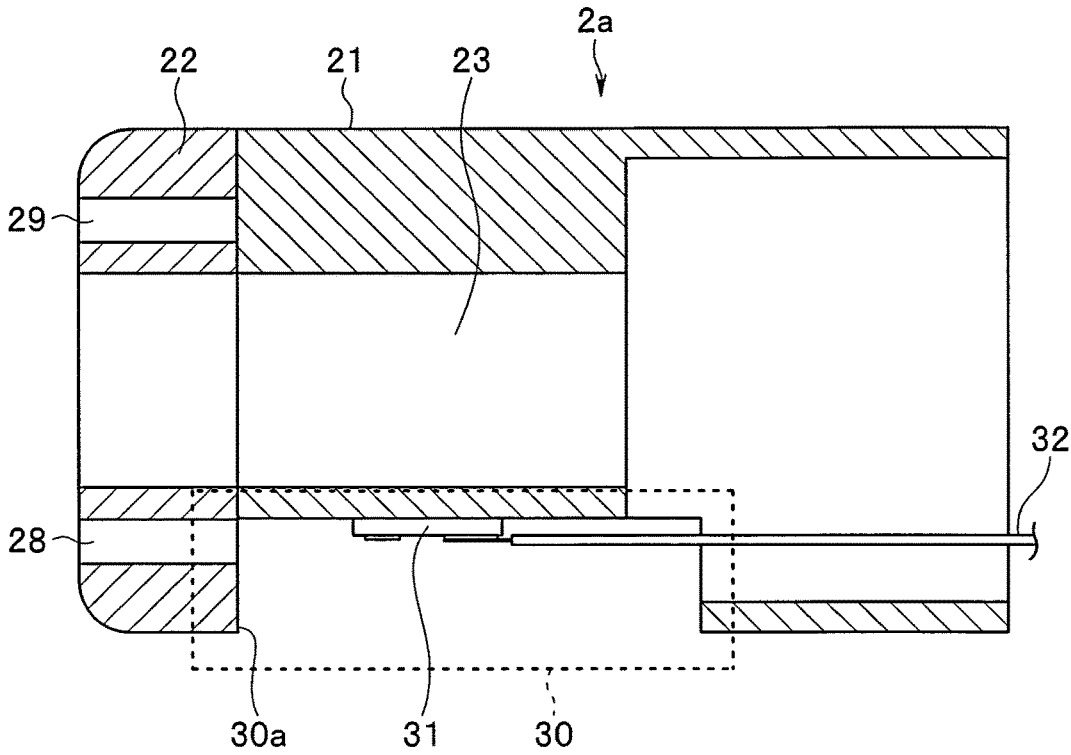
FIG. 11 is an XI-XI cross-sectional view of FIG. 12, showing an arrangement of a sensor in a distal end portion of a first example of related art.
Figure 12:
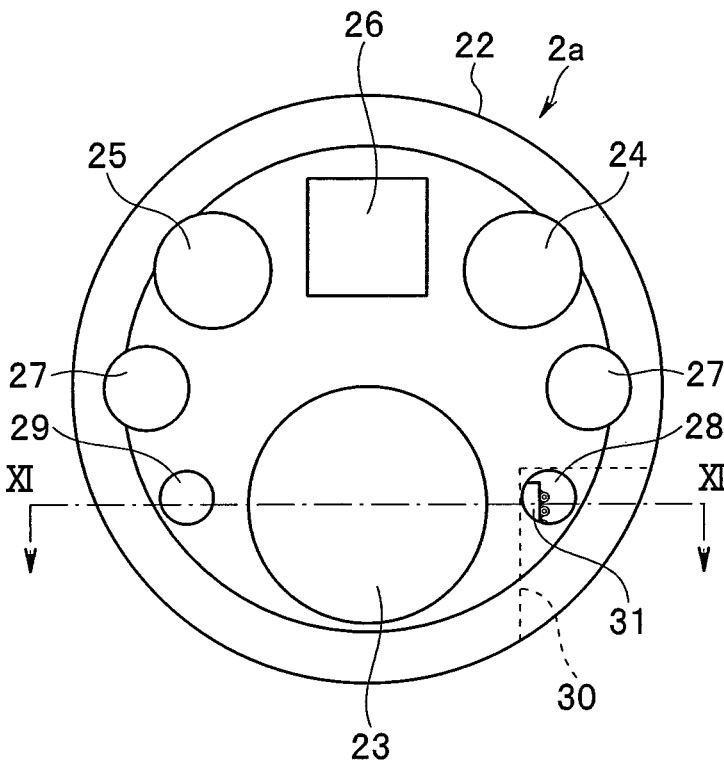
FIG. 12 is a front view showing a configuration of the distal end portion of the first example of the related art.
Figure 13:
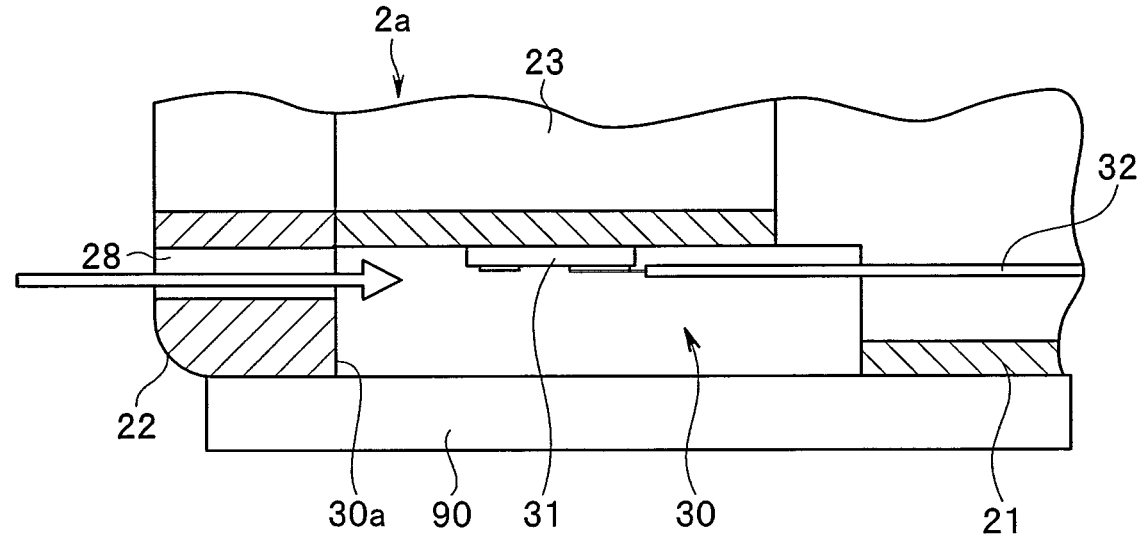
FIG. 13 is an XI-XI partial vertical cross-sectional view of FIG. 12, showing a first effect of the distal end portion of the first example of the related art.
Figure 14:
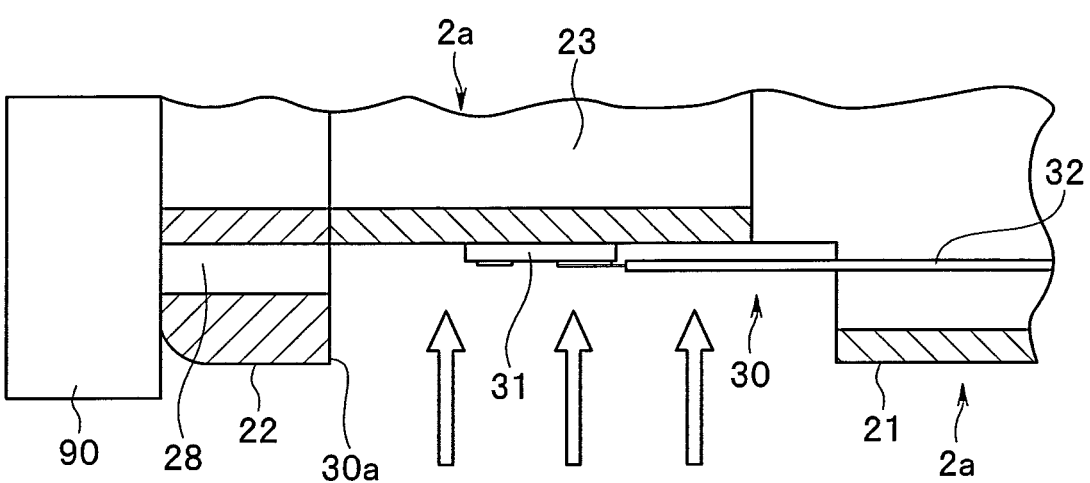
FIG. 14 is an XI-XI partial vertical cross-sectional view of FIG. 12, showing a second effect of the distal end portion of the first example of the related art.

FIGS. 11 to 14 show a first example of the related art. FIG. 11 is an XI-XI cross-sectional view of FIG. 12, showing an arrangement of a sensor 31 in the distal end portion 2a of the first example of the related art. FIG. 12 is a front view showing a configuration of the distal end portion 2a of the first example of the related art. FIG. 13 is an XI-XI partial vertical cross-sectional view of FIG. 12, showing a first effect of the distal end portion 2a of the first example of the related art. FIG. 14 is an XI-XI partial vertical cross-sectional view of FIG. 12, showing a second effect of the distal end portion 2a of the first example of the related art.

The endoscope 1 includes a conduit for guiding fluid such as liquid to the distal end side of the insertion section. The fluid that is guided by the conduit is discharged from an opening in the distal end portion 2a. In the case where the endoscope 1 is a pyeloureteroscope, fluid that is discharged from the distal end portion 2a is retained inside the subject to expand a body cavity of the subject. A field of view inside the subject is thereby expanded. Moreover, by suctioning fluid from inside the subject at the same time as discharging fluid from the distal end portion 2a, perfusion is caused inside the subject. Accordingly, stones or the like broken up by laser irradiation are carried by the perfusion, and are discharged outside the subject together with the fluid.

The distal end portion 2a includes a first distal end member 21 and a second distal end member 22. The second distal end member 22 is fixed to a distal end surface of the first distal end member 21.

The distal end portion 2a includes a suction channel 23, a liquid-feeding channel 24, a laser channel 25, the image pickup unit 26, a pair of illumination units 27, a through hole 28, a hole 29, a recessed portion 30, the sensor 31, and a signal line 32, for example.

The sensor 31 measures physical quantity inside the subject. For example, the sensor 31 is a pressure sensor that measures pressure inside the subject, or a temperature sensor that measures a temperature inside the subject. The sensor 31 is connected to the signal line 32. A signal that is outputted when physical quantity is measured by the sensor 31 is transmitted to an endoscope processor or the like through the signal line 32.

The recessed portion 30 is a part that is formed in the first distal end member 21 in a manner forming a recess (such as a cross-sectionally L-shaped recess) radially inwardly from the first distal end member 21 that is circular cylindrical shaped. The recessed portion 30 functions as a sensor arrangement part, and the sensor 31 is disposed at a position on an inside that is separate from a circumferential surface (side surface) of the circular cylindrical shape of the first distal end member 21. Such an arrangement prevents the sensor 31 from coming into contact with tissue and the like inside the subject and breaking down. The recessed portion 30 communicates with outside (outside the endoscope 1) via an opening 30a.

A distal end side of the through hole 28 is open in a distal end surface of the distal end portion 2a, and a proximal end side is open in the recessed portion 30. In other words, the through hole 28 communicates a space inside the recessed portion 30 with the outside through the distal end surface of the distal end portion 2a. The through hole 28 is used as a fluid channel (such as a water channel). The through hole 28 desirably has a diameter that is 0.2 mm or more to allow fluid to easily pass through. Note that, in FIG. 12, the through hole 28 is a circular hole, but the through hole 28 may instead have a rectangular shape or the like.

When the structure as described above is adopted, the sensor 31 communicates with the outside at two positions, that is, the side surface of the distal end portion 2a and the distal end surface of the distal end portion 2a.

FIG. 13 shows a state where tissue 90 of the subject is in contact with the side surface of the distal end portion 2a, and the opening 30a in the recessed portion 30 is blocked. Also in such a state, the sensor 31 communicates with the outside via the through hole 28. Moreover, as indicated by an arrow, fluid is able to flow into the space inside the recessed portion 30 from the outside. Accordingly, pressure and temperature inside the recessed portion 30 become the same as pressure and temperature outside, and the sensor 31 is able to accurately measure the physical quantity.

FIG. 14 shows a state where the tissue 90 of the subject is in contact with the distal end surface of the distal end portion 2a, and an opening of the through hole 28 on a distal end side is blocked. Also in such a state, the sensor 31 communicates with the outside through the opening 30a in the recessed portion 30, and as indicated by an arrow, fluid is able to flow into the space inside the recessed portion 30 from the outside. Accordingly, pressure and temperature inside the recessed portion 30 become the same as pressure and temperature outside, and the sensor 31 is able to accurately measure the physical quantity.

According to the first example of the related art, the space in the distal end portion 2a where the sensor 31 is disposed is opened in a plurality of different surfaces of the distal end portion 2a, such as the side surface and the distal end surface of the distal end portion 2a. Accordingly, even when one opening is blocked by the tissue 90 of the subject or the like, the physical quantity can be stably measured based on the fluid flowing in through the other opening. A procedure by the endoscope 1 can be accurately performed based on the physical quantity that is stably measured.

Second Example of Related Art

Figure 15:
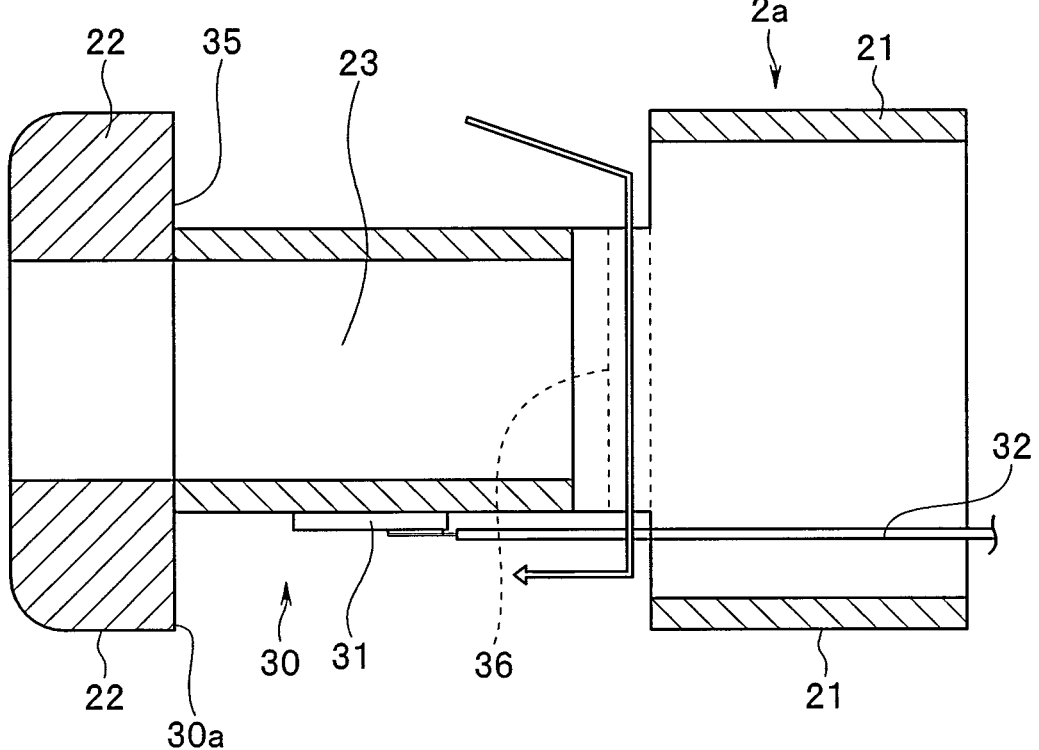
FIG. 15 is an XV-XV cross-sectional view of FIG. 16, showing an arrangement of the sensor in a distal end portion of a second example of the related art.
Figure 16:
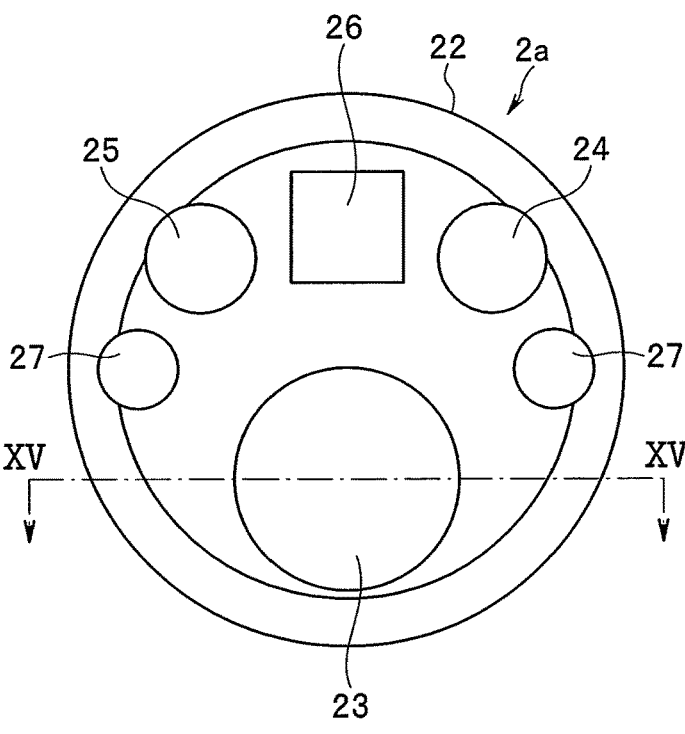
FIG. 16 is a front view showing a configuration of the distal end portion of the second example of the related art.
Figure 17:
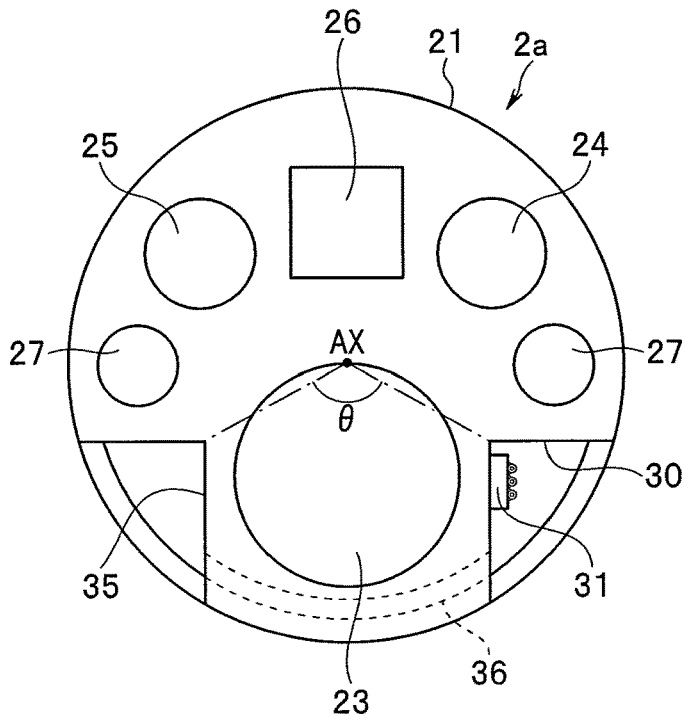
FIG. 17 is a front view showing a first distal end member of the distal end portion of the second example of the related art.

FIGS. 15 to 17 show a second example of the related art. FIG. 15 is an XV-XV cross-sectional view of FIG. 16, showing an arrangement of the sensor 31 in the distal end portion 2a of a second example of the related art. FIG. 16 is a front view showing a configuration of the distal end portion 2a of the second example of the related art. FIG. 17 is a front view showing the first distal end member 21 of the distal end portion 2a of the second example of the related art.

The distal end portion 2a of the second example of the related art further includes a second recessed portion 35 and a connection hole 36. Moreover, the through hole 28 and the hole 29 are omitted from the distal end portion 2a.

As shown in FIG. 17, the second recessed portion 35 is a part that is formed in the first distal end member 21 in a manner forming a recess (such as a cross-sectionally L-shaped recess) radially inwardly from the first distal end member 21 that is circular cylindrical shaped.

The connection hole 36 is provided circumventing the suction channel 23 and the like, and the connection hole 36 allows the recessed portion 30 and the second recessed portion 35 to communicate with each other. The connection hole 36 is a fluid channel that connects the recessed portion 30 and the second recessed portion 35. Note that the connection hole 36 joins the recessed portion 30 and the second recessed portion 35 while maintaining watertightness and airtightness with respect to internal components in the distal end portion 2a.

As shown in FIG. 17, the second recessed portion 35 is disposed at a position that forms an angle θ with the recessed portion 30 around the longitudinal axis AX passing through a center of the distal end portion 2a. The angle θ is 90 degrees or more, and is preferably 180 degrees.

Note that a second sensor that measures the same physical quantity as the sensor 31 may be disposed inside the second recessed portion 35. Alternatively, a second sensor that measures a different physical quantity from the sensor 31 may be disposed inside the second recessed portion 35.

For example, even when the opening 30a in the recessed portion 30 is blocked by the tissue 90 of the subject, the sensor 31 communicates with the outside via the connection hole 36 and the second recessed portion 35. Accordingly, as indicated by an arrow in FIG. 15, fluid is able to flow into the space inside the recessed portion 30 where the sensor 31 is disposed, from the outside. Accordingly, pressure and temperature inside the recessed portion 30 become the same as pressure and temperature outside, and the sensor 31 is able to accurately measure the physical quantity.

According to the second example of the related art, the space in the distal end portion 2a where the sensor 31 is disposed is opened at a plurality of positions on the side surface of the distal end portion 2a, at different angles around the longitudinal axis AX. Also with such a configuration of the second example, approximately the same effects as the first example described above can be obtained.

Third Example of Related Art

Figure 18:
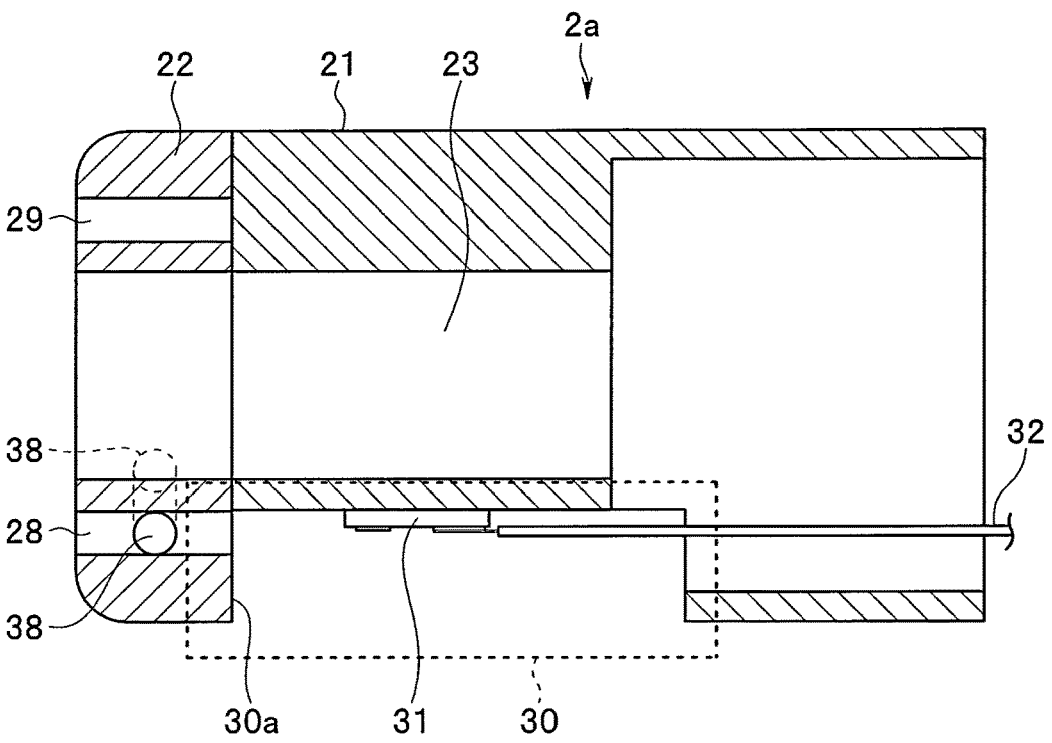
FIG. 18 is an XVIII-XVIII cross-sectional view of FIG. 19, showing an arrangement of the sensor in a distal end portion of a third example of the related art.
Figure 19:
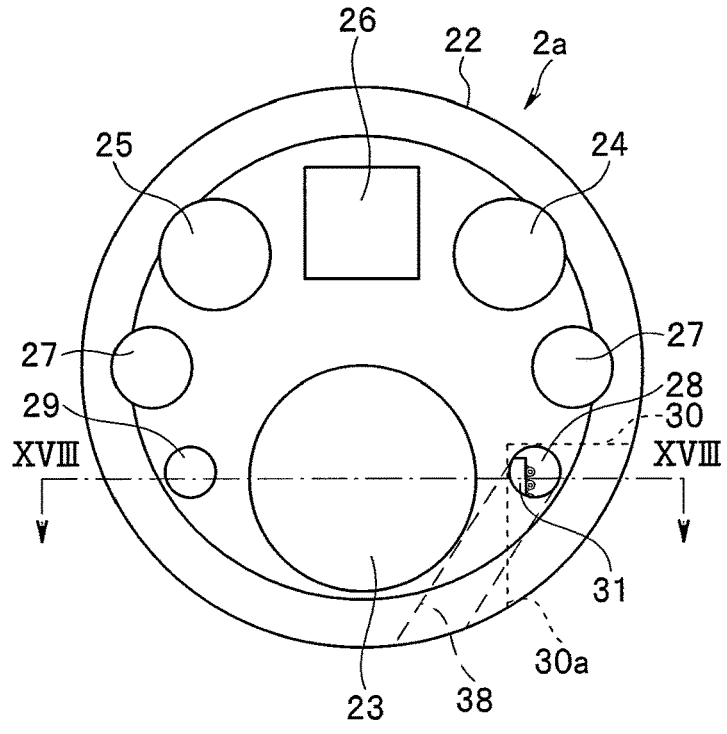
FIG. 19 is a front view showing a configuration of the distal end portion of the third example of the related art.

FIGS. 18 and 19 show a third example of the related art. FIG. 18 is an XVIII-XVIII cross-sectional view of FIG. 19, showing an arrangement of the sensor 31 in the distal end portion 2a of the third example of the related art. FIG. 19 is a front view showing a configuration of the distal end portion 2a of the third example of the related art.

The through hole 28 provided in the second distal end member 22 communicates with a branched hole 38 at a middle. The branched hole 38 is opened in the side surface of the distal end portion 2a at an angle position different from the opening 30a in the recessed portion 30. Here, an opening of the branched hole 38 and the opening 30a in the recessed portion 30 preferably form an angle of 90 degrees or more in the front view shown in FIG. 19.

According to the third example of the related art, approximately the same effects as the first example and the second example described above can be obtained. Furthermore, according to the third example of the related art, the space in the distal end portion 2a where the sensor 31 is disposed communicates with the outside through three openings in a plurality of different surfaces of the distal end portion 2a. Accordingly, possibility of all the three openings being blocked by the tissue 90 of the subject or the like is reduced, and the physical quantity can be more stably measured by the sensor 31.

Note that a description is given above mainly of a case where the present disclosure is the bending tube and the insertion appliance, but such a case is not restrictive. For example, the present disclosure may be a manufacturing method of the bending tube by which the bending tube is manufactured in the manner described above.

The present disclosure is not limited to the embodiment described above. The present disclosure can be embodied in the implementation phases by modifying structural elements without departing from the gist of the disclosure. Furthermore, various aspects of the disclosure may be implemented by combining as appropriate a plurality of structural elements disclosed in the embodiment described above. For example, several structural elements may be removed from all the structural elements disclosed in the embodiment. Moreover, structural elements of different embodiments may be combined as appropriate. In this manner, various modifications and applications are, of course, possible within the scope of the disclosure.

[Supplement 1]

A bending tube that is a rigid, cylindrical bending tube that is disposed in a bending portion of an insertion appliance, the bending tube including:

three guiding shape portions provided on an inner circumferential side of the bending tube in a direction of a longitudinal axis of the bending tube, the three guiding shape portions being provided at different positions in a circumferential direction around the longitudinal axis, the three guiding shape portions allowing insertion, respectively, of three long members that are pulled at a time of bending of the bending tube;

a first region on a distal end side in the direction of the longitudinal axis;

a second region on a proximal end side in the direction of the longitudinal axis;

a first slot that is provided in the first region and that extends in the circumferential direction, where there are four types of first slots, center positions of which in the circumferential direction are in four directions that are different from each other by 90 degrees in the circumferential direction, where each type is provided in plurality in the direction of the longitudinal axis; and a second slot that is provided in the second region and that extends in the circumferential direction, where there are two types of second slots, center positions of which in the circumferential direction are in two directions that are different from each other by 180 degrees in the circumferential direction, where each type is provided in plurality in the direction of the longitudinal axis, where a range of the first slot in the circumferential direction is greater than a range of the second slot in the circumferential direction.

[Supplement 2]

The bending tube according to Supplement 1, where the range of the first slot in the circumferential direction is greater than 180 degrees, and the range of the second slot in the circumferential direction is 180 degrees or less.

[Supplement 3]

The bending tube according to Supplement 2, where the second region includes a first partial region where the range of the second slot in the circumferential direction is 180 degrees, and a second partial region where the range of the second slot in the circumferential direction is less than 180 degrees.

[Supplement 4]

The bending tube according to Supplement 3, where the first partial region is provided on the distal end side in the direction of the longitudinal axis, and the second partial region is provided on the proximal end side in the direction of the longitudinal axis.

[Supplement 5]

The bending tube according to Supplement 3, where the range of the first slot in the circumferential direction is 206 degrees or more, and the range of the second slot in the circumferential direction is, in the second partial region, 154 degrees or less.

[Supplement 6]

The bending tube according to Supplement 1, where the first region and the second region have different lengths in the direction of the longitudinal axis.

[Supplement 7]

The bending tube according to Supplement 1, where center positions, in the circumferential direction, of two types among the four types of the first slots are same as center positions, in the circumferential direction, of the two types of the second slots.

[Supplement 8]

The bending tube according to Supplement 1, where at least the plurality of first slots or the plurality of second slots include branched slots, where one side of the branched slot in the circumferential direction is branched to reach end parts.

[Supplement 9]

The bending tube according to Supplement 8, where another side, in the circumferential direction, of the branched slot, the one side of which in the circumferential direction is branched to reach the end parts, is also branched to reach end parts.

[Supplement 10]

The bending tube according to Supplement 9, where a part of the branched slot that is branched forms a curve in a plan view obtained by spreading the bending tube.

[Supplement 11]

The bending tube according to Supplement 10, where at least the plurality of first slots or the plurality of second slots including the branched slots further include linear slots having a linear shape in the plan view obtained by spreading the bending tube.

[Supplement 12]

The bending tube according to Supplement 11, where center positions, in the circumferential direction, of the branched slot and the linear slot are provided at same positions in the direction of the longitudinal axis.

[Supplement 13]

The bending tube according to Supplement 1, where an area of the first slot is greater than an area of the second slot.

[Supplement 14]

The bending tube according to Supplement 1, where the first region and the second region of the bending tube are integrally formed by forming the first slot and the second slot in one metal pipe by laser processing.

[Supplement 15]

The bending tube according to Supplement 1, where three sets of two of the three guiding shape portions all form different angles in the circumferential direction.

[Supplement 16]

An insertion appliance including:

an insertion section configured to be inserted in a subject; and a bending portion provided at the insertion section, on a distal end side, where the bending portion includes a rigid, cylindrical bending tube, and there long members configured to be pulled at a time of bending of the bending tube, and the bending tube includes three guiding shape portions provided on an inner circumferential side of the bending tube in a direction of a longitudinal axis of the bending tube, the three guiding shape portions being provided at different positions in a circumferential direction around the longitudinal axis, the three guiding shape portions allowing insertion of the three long members, respectively, a first region on a distal end side in the direction of the longitudinal axis, a second region on a proximal end side in the direction of the longitudinal axis, a first slot that is provided in the first region and that extends in the circumferential direction, where there are four types of first slots, center positions of which in the circumferential direction are in four directions that are different from each other by 90 degrees in the circumferential direction, where each type is provided in plurality in the direction of the longitudinal axis, and a second slot that is provided in the second region and that extends in the circumferential direction, where there are two types of second slots, center positions of which in the circumferential direction are in two directions that are different from each other by 180 degrees in the circumferential direction, where each type is provided in plurality in the direction of the longitudinal axis, where a range of the first slot in the circumferential direction is greater than a range of the second slot in the circumferential direction.

[Supplement 17]

The insertion appliance according to Supplement 16, where none of positions of the three guiding shape portions in the circumferential direction matches the four directions, and two long members among the three long members are pulled at a time of bending the first region in one of the four directions.

[Supplement 18]

The insertion appliance according to Supplement 16, where the three long members are first, second, and third long members, the four directions are first, second, third, and fourth directions, where the first direction and the third direction are opposite directions, and the second direction and the fourth direction are opposite directions, the first long member and the third long member are pulled at a time of bending the first region in the first direction, the first long member and the second long member are pulled at a time of bending the first region in the second direction, the second long member and the third long member are pulled at a time of bending the first region in the third direction, the first long member and the third long member are pulled at a time of bending the first region in the fourth direction, and a ratio of an amount of pull on the third long member to an amount of pull on the first long member is different between a case of bending the first region in the first direction and a case of bending the first region in the fourth direction.

[Supplement 19]

The insertion appliance according to Supplement 16, where the insertion appliance is a single-use endoscope that is disposed of after being used once.

[Supplement 20]

A manufacturing method of a bending tube is a manufacturing method of a rigid, cylindrical bending tube that is disposed in a bending portion of an insertion appliance, the manufacturing method including:

providing, on an inner circumferential side of the bending tube, three guiding shape portions in a direction of a longitudinal axis of the bending tube, at different positions in a circumferential direction around the longitudinal axis, the three guiding shape portions allowing insertion, respectively, of three long members that are pulled at a time of bending of the bending tube;

providing, in a first region on a distal end side in a direction of the longitudinal axis, a first slot that extends in the circumferential direction, where there are provided four types of first slots, center positions of which in the circumferential direction are in four directions that are different from each other by 90 degrees in the circumferential direction, where each type is provided in plurality in the direction of the longitudinal axis; and providing, in a second region on a proximal end side in the direction of the longitudinal axis, a second slot that extends in the circumferential direction, where there are two types of second slots, center positions of which in the circumferential direction are in two directions that are different from each other by 180 degrees in the circumferential direction, where each type is provided in plurality in the direction of the longitudinal axis, where the first slot and the second slot are provided in such a way that a range of the first slot in the circumferential direction is greater than a range of the second slot in the circumferential direction, and providing the three guiding shape portions, providing the first slot, and providing the second slot are performed in any order, or any two or more are performed in parallel.

What is claimed is:

1. A bending tube of an insertion appliance, comprising:
a first region including a first plurality of slits;
a second region provided proximally relative to the first region, the second region including a second plurality of slits; and
a first guiding surface on an inner circumferential surface of the bending tube, the first guiding surface extending in a circumferential direction of the bending tube and including a channel configured to slidably house a wire for bending the bending tube,
wherein each slit of the first plurality of slits is at a different position in the circumferential direction of the bending tube, and at a different position in a longitudinal direction of the bending tube than another of the first plurality of slits,
wherein each slit of the second plurality of slits is at a different position in the circumferential direction of the bending tube, and at a different position in the longitudinal direction of the bending tube than another of the second plurality of slits,
wherein the first plurality of slits is distributed over a first angle in the circumferential direction of the bending tube, the second plurality of slits is distributed over a second angle in the circumferential direction of the bending tube, and the second angle is less than the first angle,
wherein the bending tube further comprises a second guiding surface and a third guiding surface,
wherein the first plurality of slits includes a first slit including a first center position, a second slit including a second center position, a third slit including a third center position, and a fourth slit including a fourth center position, and
wherein, in the circumferential direction of the bending tube, the first guiding surface, the second guiding surface, and the third guiding surface are at positions different from the first center position, the second center position, the third center position, and the fourth center position.

2. The bending tube according to claim 1, wherein the first angle is greater than 180 degrees and the second angle is 180 degrees or less.

3. The bending tube according to claim 1, further comprising a third region including a third plurality of slits, wherein the first region, the second region, and the third region are arranged along the longitudinal direction of the bending tube with the second region between the first region and the third region, wherein each slit of the third plurality of slits is at a different position in the circumferential direction of the bending tube, and is at a different position in the longitudinal direction of the bending tube than another of the third plurality of slits, wherein the third plurality of slits is distributed over a third angle in the circumferential direction of the bending tube, and wherein the second angle is greater than the third angle.

4. The bending tube according to claim 3, wherein the first angle is 206 degrees or more, and the third angle is 154 degrees or less.

5. The bending tube according to claim 1, wherein the first region and the second region have different lengths in the longitudinal direction of the bending tube.

6. The bending tube according to claim 1, wherein the first plurality of slits including a first slit and a second slit, wherein the second plurality of slits include including a third slit and a fourth slit, and wherein, in the circumferential direction of the bending tube:

a center position of the first slit and a center position of the third slit are the same, and a center position of the second slit and a center position of the fourth slit are the same.

7. The bending tube according to claim 1, wherein the first plurality of slits include a first slit, wherein the second plurality of slits include a second slit, and wherein at least one of the first slit and the second slit includes a first branched portion.

8. The bending tube according to claim 7, wherein at least one of the first slit and the second slit includes a second branched portion.

9. The bending tube according to claim 8, wherein at least one of the first region and the second region further includes a third slit having a linear shape.

10. The bending tube according to claim 9, wherein, in the longitudinal direction of the bending tube, at least one of the first slit and the second slit is at a same position as the third slit.

11. The bending tube according to claim 1, wherein the first plurality of slits including a first slit, wherein the second plurality of slits include a second slit, and wherein an area of the first slit is greater than an area of the second slit.

12. The bending tube according to claim 1, wherein a first distance between the first guiding surface and the second guiding surface is different from a second distance between the first guiding surface and the third guiding surface.

13. The bending tube according to claim 1, wherein the first plurality of slits includes first, second, third, and fourth slits, and wherein the second plurality of slits includes fifth and sixth slits.

14. The bending tube according to claim 13, wherein the first, second, third, and fourth slits are provided in plurality, and repeatedly provided in the longitudinal direction of the bending tube, in an order of the first, second, third, and fourth slits, and wherein the plurality of fifth and sixth slits are provided in plurality, and repeatedly provided in the longitudinal direction of the bending tube, in an order of the fifth and sixth slits.

15. The bending tube according to claim 13, wherein the first, second, third, and fourth slits are separated from each other in the circumferential direction of the bending tube by 90 degrees, and wherein the fifth and sixth slits are separated from each other in the circumferential direction of the bending tube by 180 degrees.

16. An insertion appliance, comprising:

an insertion section including a bending tube, wherein the bending tube includes:

a first region including a first plurality of slits;

a second region including a second plurality of slits, the second region separated from the first region along a longitudinal axis of the bending tube;

a first guiding surface on an inner circumferential surface of the bending tube, the first guiding surface extending in a circumferential direction of the bending tube and including a first channel; and a first wire slidably housed in the first channel, the first wire configured for bending the bending tube, wherein each slit of the first plurality of slits is at a different position in the circumferential direction of the bending tube, and is at a different position in a longitudinal direction of the bending tube than another of the first plurality of slits, wherein each slit of the second plurality of slits is at a different position in the circumferential direction of the bending tube, and is at a different position in the longitudinal direction of the bending tube than another slit of the second plurality of slits, wherein the first plurality of slits is distributed over a first angle in the circumferential direction of the bending tube, the second plurality of slits is distributed over a second angle in the circumferential direction of the bending tube, and the second angle is less than the first angle, wherein the bending tube further includes a second guiding surface including a second channel, a third guiding surface including a third channel, a second wire slidably housed in the second channel, and a third wire slidably housed in the third channel, wherein the first plurality of slits includes a first slit, a second slit, a third slit, and a fourth slit, wherein, relative to a longitudinal axis of the insertion section, the first slit and the third slit are positioned opposite each other and the second slit and the fourth slit are positioned opposite each other, wherein:

when the first wire is pulled by a first pulling distance and the third wire is pulled by a second pulling distance, the first region bends in a first direction, when the first wire and the second wire are pulled, the first region bends in a second direction, when the second wire and the third wire are pulled, the first region bends in a third direction, and when the first wire is pulled by a third pulling distance and the third wire is pulled by a fourth pulling distance, the first region bends in a fourth direction, and wherein a ratio between the first pulling distance and the second pulling distance is different from a ratio between the third pulling distance and the fourth pulling distance.

17. The insertion appliance according to claim 16, wherein the insertion appliance is a single-use endoscope.

18. A manufacturing method of a bending tube of an insertion appliance, the manufacturing method comprising:

provide a first guiding surface, a second guiding surface, and a third guiding surface on an inner circumferential surface of the bending tube, wherein the first guiding surface, the second guiding surface, and the third guiding surface, are distributed in a circumferential direction of the bending tube, and wherein the first guiding surface includes a first channel configured to slidably house a first wire for bending the bending tube the second guiding surface includes a second channel configured to slidably house a second wire for bending the bending tube, and the third guiding surface includes a third channel configured to slidably house a third wire for bending the bending tube;

providing, in a first region of the bending tube, a first plurality of slits, wherein each slit of the first plurality of slits at different positions in the circumferential direction of the bending tube, and at different positions in a longitudinal direction of the bending tube than another of the first plurality of slits; and providing, in a second region, a second plurality of slits, wherein each slit of the second plurality of slits is at different positions in the circumferential direction of the bending tube, and at different positions in the longitudinal direction of the bending tube than another of the second plurality of slits, wherein the second region is provided proximally relative to the first region, wherein the first plurality of slits is distributed over a first angle in the circumferential direction of the bending tube, the second plurality of slits is distributed over a second angle in the circumferential direction of the bending tube, and the second angle is less than the first angle, wherein the first plurality of slits includes a first slit including a first center position, a second slit including a second center position, a third slit including a third center position, and a fourth slit including a fourth center position, and wherein, in the circumferential direction, the first guiding surface, the second guiding surface, and the third guiding surface are at positions different from the first center position, the second center position, the third center position, and the fourth center position.

19. An insertion appliance, comprising:

an insertion section including the bending tube according to claim 1.

* * * * *